(12) United States Patent
Jodaitis et al.

(10) Patent No.: US 8,685,100 B2
(45) Date of Patent: Apr. 1, 2014

(54) INTERVETERBRAL DISC PROSTHESIS INSERTION ASSEMBLIES

(75) Inventors: Alexandre Jodaitis, Morlanwelz (BE); Herve Dinville, St-Parres-aux-Tertres (FR); Alexis Mercier, Troyes (FR)

(73) Assignee: LDR Medical, Rosieres Pres Troyes (FR)

( * ) Notice: Subject to any disclaimer, the term of this patent is extended or adjusted under 35 U.S.C. 154(b) by 343 days.

(21) Appl. No.: 12/527,373

(22) PCT Filed: Feb. 15, 2008

(86) PCT No.: PCT/IB2008/000349
§ 371 (c)(1),
(2), (4) Date: Mar. 19, 2010

(87) PCT Pub. No.: WO2008/099277
PCT Pub. Date: Aug. 21, 2008

(65) Prior Publication Data
US 2010/0280618 A1    Nov. 4, 2010

Related U.S. Application Data

(63) Continuation of application No. 11/676,237, filed on Feb. 16, 2007, now Pat. No. 8,465,546.

(51) Int. Cl.
*A61F 2/44*    (2006.01)

(52) U.S. Cl.
USPC .......................................... 623/17.16; 606/99

(58) Field of Classification Search
USPC ..................... 606/99, 86 A; 623/17.11–17.16
See application file for complete search history.

(56) References Cited

U.S. PATENT DOCUMENTS

| 4,655,778 A | 4/1987 | Koeneman |
| 4,756,711 A | 7/1988 | Mai et al. |

(Continued)

FOREIGN PATENT DOCUMENTS

| DE | 2263842 | 7/1974 |
| DE | 2804936 | 8/1979 |

(Continued)

OTHER PUBLICATIONS

U.S. Appl. No. 10/498,234, filed Dec. 7, 2004, Implant for Osseous Anchoring with Polyaxial Head.

(Continued)

*Primary Examiner* — Jan Christopher Merene
*Assistant Examiner* — Steven Cotroneo
(74) *Attorney, Agent, or Firm* — Denko Coburn Lauff LLP

(57) ABSTRACT

In various embodiments, an intervertebral disc prosthesis (104) is provided. The prosthesis (104) may be provided with an insertion adapter (106), such as a head, holder, or other carrier of the prosthesis (104). The insertion adapter (106) may be configured to retain the prosthesis (104) and to engage an insertion tool body (130). In various embodiments, the prosthesis (104) and the insertion holder are provided in a sterile pack (102, 202), with the prosthesis (104) components and the insertion holder sterilized and packaged in one or more types or layers of sterile packaging (103a, 103b). In various other embodiments, the prosthesis (104) and an insertion tool (131) are provided in a sterile pack (102, 202), with the prosthesis (104) components and the insertion tool (131) sterilized and packaged in one or more types or layers of sterile packaging (103a, 103b).

20 Claims, 20 Drawing Sheets

(56) References Cited

U.S. PATENT DOCUMENTS

| | | |
|---|---|---|
| 4,759,766 A | 7/1988 | Buettner-Janz et al. |
| 4,759,769 A | 7/1988 | Hedman et al. |
| 4,787,908 A | 11/1988 | Wyss et al. |
| 4,863,476 A | 9/1989 | Shepperd |
| 4,874,389 A | 10/1989 | Downey |
| 4,892,545 A | 1/1990 | Day et al. |
| 4,946,378 A | 8/1990 | Hirayama et al. |
| 4,955,916 A | 9/1990 | Carignan et al. |
| 4,997,432 A | 3/1991 | Keller |
| 5,002,576 A | 3/1991 | Fuhrmann et al. |
| 5,041,139 A | 8/1991 | Branemark |
| 5,071,437 A | 12/1991 | Steffee |
| 5,122,130 A | 6/1992 | Keller |
| 5,192,327 A | 3/1993 | Brantigan |
| 5,197,986 A | 3/1993 | Mikhail |
| 5,246,458 A | 9/1993 | Graham |
| 5,258,031 A | 11/1993 | Salib et al. |
| 5,290,312 A | 3/1994 | Kojimoto et al. |
| 5,306,309 A | 4/1994 | Wagner et al. |
| 5,314,477 A | 5/1994 | Marnay |
| 5,358,526 A | 10/1994 | Tornier |
| 5,370,697 A | 12/1994 | Baumgartner |
| 5,401,269 A | 3/1995 | Buttner-Janz et al. |
| 5,425,773 A | 6/1995 | Boyd et al. |
| 5,443,514 A | 8/1995 | Steffee |
| 5,507,816 A | 4/1996 | Bullivant |
| 5,534,030 A | 7/1996 | Navarro et al. |
| 5,545,229 A | 8/1996 | Parsons et al. |
| 5,556,431 A | 9/1996 | Buttner-Janz et al. |
| 5,562,738 A | 10/1996 | Boyd et al. |
| 5,571,109 A | 11/1996 | Bertagnoli |
| 5,609,636 A | 3/1997 | Kohrs et al. |
| 5,674,294 A | 10/1997 | Bainville et al. |
| 5,676,701 A | 10/1997 | Yuan et al. |
| 5,683,465 A | 11/1997 | Shinn et al. |
| 5,782,832 A | 7/1998 | Larsen et al. |
| 5,824,094 A | 10/1998 | Serhan et al. |
| 5,865,848 A | 2/1999 | Baker |
| 5,888,226 A | 3/1999 | Rogozinski |
| 5,893,889 A | 4/1999 | Harrington |
| 5,895,428 A | 4/1999 | Berry |
| 5,899,941 A | 5/1999 | Nishijima et al. |
| 6,010,502 A | 1/2000 | Bagby |
| 6,045,552 A | 4/2000 | Zucherman et al. |
| 6,063,121 A | 5/2000 | Xavier et al. |
| 6,096,080 A | 8/2000 | Nicholson et al. |
| 6,113,637 A | 9/2000 | Gill et al. |
| 6,146,421 A | 11/2000 | Gordon et al. |
| 6,179,873 B1 | 1/2001 | Zientek |
| 6,344,057 B1 | 2/2002 | Rabbe et al. |
| 6,368,350 B1 | 4/2002 | Erickson et al. |
| 6,402,785 B1 | 6/2002 | Zdeblick et al. |
| 6,413,278 B1 | 7/2002 | Marchosky |
| 6,419,706 B1 | 7/2002 | Graf |
| 6,447,546 B1 | 9/2002 | Bramlet et al. |
| 6,506,216 B1 | 1/2003 | McCue et al. |
| 6,540,753 B2 | 4/2003 | Cohen |
| 6,636,071 B1 | 10/2003 | Yatabe |
| 6,641,614 B1 | 11/2003 | Wagner et al. |
| 6,899,735 B2 | 5/2005 | Coates et al. |
| 6,994,727 B2 | 2/2006 | Khandkar et al. |
| 7,037,340 B2 | 5/2006 | Gau |
| 7,056,344 B2 | 6/2006 | Huppert et al. |
| 7,060,097 B2 | 6/2006 | Fraser et al. |
| 7,147,665 B1 | 12/2006 | Bryan et al. |
| 7,217,292 B2 * | 5/2007 | Ralph et al. ............... 623/17.16 |
| 7,291,170 B2 | 11/2007 | Huppert |
| 7,326,250 B2 | 2/2008 | Beaurain et al. |
| 7,419,505 B2 * | 9/2008 | Fleischmann et al. ...... 623/17.11 |
| 7,481,840 B2 | 1/2009 | Zuckerman et al. |
| 7,494,507 B2 | 2/2009 | Dixon et al. |
| 7,494,508 B2 | 2/2009 | Zeegers |
| 7,507,248 B2 | 3/2009 | Beaurain et al. |
| 7,517,363 B2 | 4/2009 | Rogers et al. |
| 7,575,599 B2 | 8/2009 | de Villiers et al. |
| 7,575,600 B2 | 8/2009 | Zuckerman et al. |
| 7,594,931 B2 | 9/2009 | Louis et al. |
| 7,611,538 B2 | 11/2009 | Belliard et al. |
| 7,621,956 B2 | 11/2009 | Paul et al. |
| 7,632,282 B2 | 12/2009 | Dinville |
| 7,682,396 B2 | 3/2010 | Beaurain et al. |
| 7,695,516 B2 | 4/2010 | Zeegers |
| 7,695,518 B2 | 4/2010 | Gau |
| 7,708,776 B1 | 5/2010 | Blain et al. |
| 7,717,959 B2 | 5/2010 | William et al. |
| 7,771,478 B2 | 8/2010 | Navarro et al. |
| 7,842,088 B2 | 11/2010 | Rashbaum et al. |
| 7,896,919 B2 | 3/2011 | Belliard et al. |
| 8,002,835 B2 | 8/2011 | Zeegers |
| 8,147,556 B2 | 4/2012 | Louis et al. |
| 8,162,988 B2 | 4/2012 | Delecrin et al. |
| 8,221,422 B2 | 7/2012 | Mangione |
| 8,221,457 B2 | 7/2012 | Delecrin et al. |
| 8,241,359 B2 | 8/2012 | Davis et al. |
| 8,257,439 B2 | 9/2012 | Zeegers |
| 8,262,700 B2 | 9/2012 | Cho et al. |
| 8,267,999 B2 | 9/2012 | Beaurain et al. |
| 8,343,219 B2 | 1/2013 | Allain et al. |
| 8,388,684 B2 | 3/2013 | Bao et al. |
| 8,409,288 B2 | 4/2013 | Davis et al. |
| 8,430,915 B2 | 4/2013 | Beaurain et al. |
| 8,439,931 B2 | 5/2013 | Dinville |
| 8,465,546 B2 | 6/2013 | Jodaitis et al. |
| 2002/0035400 A1 | 3/2002 | Bryan et al. |
| 2003/0069586 A1 * | 4/2003 | Errico et al. ............... 606/99 |
| 2004/0010316 A1 | 1/2004 | William et al. |
| 2004/0117022 A1 | 6/2004 | Marnay et al. |
| 2004/0243238 A1 | 12/2004 | Arnin et al. |
| 2004/0243240 A1 | 12/2004 | Beaurain et al. |
| 2005/0027359 A1 | 2/2005 | Mashburn |
| 2005/0027363 A1 | 2/2005 | Gordon |
| 2005/0038516 A1 | 2/2005 | Spoonamore |
| 2005/0060034 A1 | 3/2005 | Berry et al. |
| 2005/0085917 A1 | 4/2005 | Marnay et al. |
| 2005/0149189 A1 | 7/2005 | Mokhtar et al. |
| 2005/0197706 A1 * | 9/2005 | Hovorka et al. ........... 623/17.15 |
| 2006/0030860 A1 * | 2/2006 | Peterman ................... 606/99 |
| 2006/0041314 A1 | 2/2006 | Millard |
| 2006/0069437 A1 | 3/2006 | Weber |
| 2006/0122703 A1 | 6/2006 | Aebi et al. |
| 2006/0155377 A1 | 7/2006 | Beaurain et al. |
| 2006/0259147 A1 | 11/2006 | Krishna et al. |
| 2007/0088362 A1 * | 4/2007 | Bonutti et al. ............. 606/99 |
| 2007/0162130 A1 * | 7/2007 | Rashbaum et al. ........ 623/17.11 |

FOREIGN PATENT DOCUMENTS

| | | |
|---|---|---|
| DE | 3023353 | 4/1981 |
| EP | 42271 | 12/1981 |
| EP | 176728 | 4/1986 |
| EP | 333990 | 9/1989 |
| FR | 2124815 | 9/1972 |
| FR | 2372622 | 6/1978 |
| FR | 2718635 | 10/1995 |
| FR | 2737656 | 2/1997 |
| FR | 2 865 629 | 5/2005 |
| FR | 2 846 550 | 4/2007 |
| FR | 2893838 | 6/2007 |
| FR | 2 824 261 | 2/2008 |
| JP | 2261446 | 10/1990 |
| WO | WO0289701 | 11/2002 |
| WO | WO2004041129 | 5/2004 |
| WO | WO2005007044 | 1/2005 |
| WO | WO2005074839 | 8/2005 |
| WO | WO2007063398 | 6/2007 |

OTHER PUBLICATIONS

U.S. Appl. No. 10/570,080, filed Jun. 9, 2006, Osseous anchoring implant with a polyaxial head and method for installing the implant.
U.S. Appl. No. 11/051,710, filed Feb. 4, 2005, Intervertebral Disc Prosthesis.
U.S. Appl. No. 11/362,253, filed Feb. 24, 2006, Intervertebral Disc Prosthesis and Instrumentation for Insertion of the Prosthesis Between the Vertebrae.

(56) References Cited

OTHER PUBLICATIONS

U.S. Appl. No. 11/767,386, filed Jun. 22, 2007, Intersomatic cage with unified grafts.
U.S. Appl. No. 11/874,144, filed Oct. 17, 2007, Nucleus Prostheses.
U.S. Appl. No. 11/958,285, filed Dec. 17, 2007, Vertebral Support Device.
U.S. Appl. No. 12/025,677, filed Feb. 4, 2008, Intervertebral disc prosthesis, surgical metods, and fitting tools.
U.S. Appl. No. 12/562,704, filed Sep. 18, 2009, Intervertebral Disc Prosthesis.
U.S. Appl. No. 12/955,898, filed Nov. 29, 2010, Intervertebral Disc Prosthesis.
U.S. Appl. No. 13/158,761, filed Jun. 13, 2011, Instruments and Methods for Removing Fixation Devices from Intervertebral Implants.
U.S. Appl. No. 13/215,123, filed Aug. 22, 2011, Intervertebral Disc Prosthesis.
U.S. Appl. No. 13/369,650, filed Feb. 9, 2012, Interspinous Implant and Implantation Instrument.
U.S. Appl. No. 13/438,352, filed Apr. 3, 2012, Vertebral Cage Device with Modular Fixation.
U.S. Appl. No. 13/454,927, filed Apr. 24, 2012, Plate for osteosynthesis device and method of preassembling such device.
U.S. Appl. No. 13/520,041, filed Jun. 29, 2012, Anchoring Device and System for an Intervertebral Implant, Intervertebral Implant and Implantation Instrument.
U.S. Appl. No. 13/538,078, filed Jun. 29, 2012, Anchoring Device and Syste, for an Intervertebral Implant, Intervertebral Implant and Implantation Instrument.
U.S. Appl. No. 13/585,063, filed Aug. 14, 2012, Transforaminal intersomatic cage for an intervertebral fusion graft and an instrument for implanting the cage.
U.S. Appl. No. 13/603,043, filed Sep. 4, 2012, Intervertebral Disc Prosthesis.
U.S. Appl. No. 13/616,448, filed Sep. 14, 2012, Intervertebral Disc Prosthesis.
U.S. Appl. No. 13/620,797, filed Sep. 15, 2012, Intervertebral Disc Prosthesis and Instrumentation for Insertion of the Prosthesis Between the Vertebrae.
U.S. Appl. No. 13/732,244, filed Dec. 31, 2012, Intersomatic cage, intervertebral prothesis, anchoring device and implantation instruments.
U.S. Appl. No. 13/774,547, filed Feb. 22, 2013, Anchoring device and system for an intervertebral implant, intervertebral implant and implantation instrument.
U.S. Appl. No. 13/854,808, filed Apr. 1, 2013, Transforanimal intersomatic cage for an intervertebral fusion graft and an instrument for implanting the cage.
U.S. Appl. No. 13/873,190, filed Apr. 29, 2013, Spinal Osteosynthesis Device and Preparation Method.
U.S. Appl. No. 13/892,933, filed May 13, 2013, Instrumentation and Method for Inserting an Intervertebral Disc Prosthesis.
U.S. Appl. No. 13/919,704, filed Jun. 17, 2013, Intervertebral disc prothesis insertion assemblies.
LDR Medical, by its attorneys; Reply to Office Action in U.S. Appl. No. 12/025,677; Dec. 20, 2013; USPTO; Alexandria, Virgina; All Pages.
U.S. Patent & Trademark Office; Office Action in U.S. Appl. No. 12/025,677; Jun. 20, 2013; USPTO; Alexandria, Virgina; All Pages.
LDR Medical, by its attorneys; Reply to Office Action in U.S. Appl. No. 12/025,677; Dec. 29, 2012; USPTO; Alexandria, Virgina; All Pages.
U.S. Patent & Trademark Office; Notice of Allowance in U.S. Appl. No. 12/424,364; Aug. 2, 2012; USPTO; Alexandria, Virgina; All Pages.
U.S. Patent & Trademark Office; Office Action in U.S. Appl. No. 13/616,448; Aug. 22, 2013; USPTO; Alexandria, Virgina; All Pages.
LDR Medical, by its attorneys; Requesst for Continued Examination in U.S. Appl. No. 11/051,710; Jul. 11, 2013; USPTO; Alexandria, Virgina; All Pages.
U.S. Patent & Trademark Office; Notice of Allowance in U.S. Appl. No. 11/051,710; Apr. 11, 2013; USPTO; Alexandria, Virgina; All Pages.
LDR Medical, by its attorneysl Appeal Brief in U.S. Appl. No. 11/051,710; Jan. 15, 2013; USPTO; Alexandria, Virgina; All Pages.
U.S. Patent & Trademark Office; Office Action in U.S. Appl. No. 13/215,123; Nov. 18, 2013; USPTO; Alexandria, Virgina; All Pages.
LDR Medical, by its attorneys; Reply to Office Action in U.S. Appl. No. 13/215,123; Nov. 11, 2013; USPTO; Alexandria, Virgina; All Pages.
LDR Medical, by its attorneys; Reply to Office Action in U.S. Appl. No. 13/215,123; Oct. 24, 2013; USPTO; ALexandria, Virgina; All Pages.
U.S. Patent & Trademark Office; Office Action in U.S. Appl. No. 13/215,123; May 24, 2013; USPTO; Alexandria, Virgina; All Pages.
LDR Medical, by its attorneys; Reply to Office Action in U.S. Appl. No. 13/215,123; Mar. 20, 2013; USPTO; Alexandria, Virgina; All Pages.
LDR Medical, by its attorneys; Terminal Disclaimer in U.S. Appl. No. 13/215,123; Mar. 20, 2013; USPTO; Alexandria, Virgina; All Pages.
U.S. Patent & Trademark Office; Office Action in U.S. Appl. No. 13/215,123; Nov. 20, 2012; USPTO; Alexandria, Virgina; All Pages.
U.S. Patent & Trademark Office; Notice of Allowance in U.S. Appl. No. 12/360,050; Aug. 2, 2012; USPTO; Alexandria, Virgina; All Pages.
U.S. Patent & Trademark Office; Notice of Allowance in U.S. Appl. No. 12/360,050; May 18, 2012; USPTO; Alexandria, Virgina; All Pages.
U.S. Patent & Trademark Office; Office Action in U.S Appl. No. 13/603,043; Nov. 21, 2013; USPTO; Alexandria, Virgina; All Pages.
LDR Medical, by its attorneys; Reply to Office Action in U.S. Appl. No. 13/603,043; Oct. 9, 2013; USPTO; Alexandria, Virgina; All Pages.
U.S. Patent & Trademark Office; Office Action in U.S. Appl. No. 13/603,043; Apr. 9, 2013; USPTO; ALexandria, Virgina; All Pages.
U.S. Patent & Trademark Office; Notice of Allowance in U.S. Appl. No. 12/435,955; Jan. 16, 2013;USPTO; Alexandria, Virgina; All Pages.
LDR Medical, by its attorneys; Reply to Office Action in U.S. Appl. No. 12/435,955; Dec. 24, 2012; USPTO; Alexandria, Virgina; All Pages.
U.S. Patent & Trademark Office; Office Action in U.S. Appl. No. 12/435,955; Jul. 23, 2012; USPTO; Alexandria, Virgina; All Pages.
LDR Medical, by its attorneys; Reply to Office Action in U.S. Appl. No. 12/955,898; Jul. 10, 2013; USPTO; Alexandria, Virgina; All Pages.
U.S. Patent & Trademark Office; Office Action in U.S. Appl. No. 12/955,898; Jan. 10, 2013; USPTO; Alexandria, Virgina; All Pages.
LDR Medical, by its attorneys; Reply to Office Action in U.S. Appl. No. 12/955,898; Dec. 3, 2012; USPTO; Alexandria, Virgina; All Pages.
LDR Medical, by its attorneys; Reply Brief in U.S. Appl. No. 11/362,253; Aug. 20, 2012; USPTO; Alexandria, Virgina; All Pages.
LDR Medical, by its attorneys; Reply to Office Action in U.S. Appl. No. 13/620,797; Nov. 5, 2013; USPTO; Alexandria, Virgina; All Pages.
U.S. Patent & Trademark Office; Office Action in U.S. Appl. No. 13/620,797; Jul. 5, 2013; USPTO; Alexandria, Virgina; All Pages.
U.S. Patent & Trademark Office; Notice of Allowance in U.S. Appl. No. 12/134,884; Nov. 1, 2012; USPTO; Alexandria, Virgina; All Pages.
LDR Medical, by its attorneys; Reply to Office Action in U.S. Appl. No. 12/134,884; Jul. 31, 2012; USPTO; Alexandria, Virgina; All Pages.
U.S. Patent & Trademark Office; Office Action in U.S. Appl. No. 13/919,704; Nov. 18, 2013; USPTO; Alexandria, Virgina; All Pages.
LDR Medical, by its attorneys; Reply to Office Action in U.S. Appl. No. 13/158,761; Nov. 14, 2013; USPTO; Alexandria, Virgina; All Pages.
U.S. Patent & Trademark Office; Office Action in U.S. Appl. No. 13/158,761; Aug. 14, 2013; USPTO; Alexandria, Virgina; All Pages.

(56) References Cited

OTHER PUBLICATIONS

U.S. Patent & Trademark Office; Interview Summary in U.S. Appl. No. 13/158,761; Aug. 1, 2013; USPTO; Alexandria, Virgina; All Pages.
LDR Medical, by its attorneys; Reply to Office Action in U.S. Appl. No. 13/158,761; Jul. 29, 2013; USPTO; Alexandria, Virgina; All Pages.
U.S. Patent & Trademark Office; Office Action in U.S. Appl. No. 13/158,761; Feb. 28, 2013; USPTO; Alexandria, Virgina; All Pages.
LDR Medical, by its attorneys; Reply to Office Action in U.S. Appl. No. 13/158,761; Nov. 19, 2012; USPTO; Alexandria, Virgina; All Pages.
U.S. Patent & Trademark Office; Interview Summary in U.S. Appl. No. 13/158,761; Oct. 31, 2012; USPTO; Alexandria, Virgina; All Pages.
U.S. Patent & Trademark Office; Office Action in U.S. Appl. No. 13/158,761; Oct. 17, 2012; USPTO; Alexandria, Virgina; All Pages.

* cited by examiner

INTERVETERBRAL DISC PROSTHESIS
INSERTION ASSEMBLIES

CROSS REFERENCE TO RELATED APPLICATIONS

This application is a National Stage entry of International Application No. PCT/IB08/00349 filed Feb. 14, 2008, which is a continuation of U.S. patent application No. 11/676,237 filed Feb. 16, 2007, now U.S. Patent No. 8,465,546 issued Jun. 18, 2013.

TECHNICAL FIELD

This disclosure relates to the field of prostheses and in particular to intervertebral disc prostheses for replacement of natural intervertebral discs.

BACKGROUND

A healthy intervertebral disc is flexible enough to allow movement between adjacent vertebrae or between a vertebra and another adjacent spinal column element, such as the coccyx (the most inferior portion of the vertebral column, resulting from the fusion of the four coccygeal vertebrae) and the sacrum (a triangular bone that is the posterior skeletal element forming the pelvis, formed by 5 fused vertebrae). This movement accommodates bending of the spine. Disease or degeneration of the tissues of a natural intervertebral disc often leads to intense pain and reduced mobility. When degeneration or disease of the natural intervertebral disc has progressed to the point where non-operative care such as medication, injections, and/or physical therapy is ineffective, surgical intervention may be required.

A common procedure for treatment of degenerative or diseased intervertebral discs involves removal of the natural tissues of the disc and fusion of the adjacent vertebrae. Fusion eliminates the mobility between the adjacent vertebrae, however, and can transfer stresses and movements to the intervertebral discs above and/or below the point of fusion.

Intervertebral disc prostheses have been developed to mitigate some of the problems caused by intervertebral fusion. In particular, various designs of intervertebral disc prostheses can provide a relatively normal range of movement to the adjacent vertebra, resulting in a more normal distribution of stresses and movements along the various segments of the spine. Intervertebral disc prostheses typically are configured to restore normal disc height, and can decrease surgical morbidity and complications from postoperative immobilization instrumentation typically present in fusion procedures.

The patents FR 2 824 261, FR 2 846 550 and FR 2 865 629, and the patent application FR 2 893 838 (corresponding to applications WO 02/089701, WO 04/041129, WO 2005/074839 and WO 2007063398 and to U.S. patent application Ser. Nos. 10/476,565, 10/533,846, 11/051,710, and 11/362,253), each of which is assigned to the assignee of the present application and each of which is incorporated herein by reference for all purposes, disclose various intervertebral disc prosthesis configurations. In many of these configurations, the prosthesis may have an upper plate supporting the upper vertebra, a lower plate supporting the lower vertebra, and a mobile core or nucleus that provides some range of articulation between the upper plate and the lower plate.

Prior to the surgical implantation procedure, measurements often are made of the plates of the upper and lower vertebrae to confirm the viability of the procedure. Following discectomy in various representative procedures, the depth and width of the intervertebral space are measured, and a determination is made of an appropriate vertical spacing of the adjacent vertebra and the sizes of the upper and lower disc prosthesis plates and the core.

Typically, there are several selections for the depth and width of the intervertebral prosthesis plates and for the height of the core, depending on the type of intervertebral disc prosthesis. For example, the LDR Medical Mobi-C(™) cervical disc prosthesis currently can be configured with any of 4 plate sizes and 3 core heights, and the LDR Medical Mobidisc(™) lumbar disc prosthesis currently can be configured with any of 18 plate sizes and 6 core heights. In addition, the surgeon may wish to accommodate or correct a lordosis or kyphosis by using one or more plates having an angular offset between the vertebral axis implied by a normal to the plate's vertebral contact surface and a mean, or neutral, normal axis implied by the plate's core contact surface. Thus, even within a single product line, there may be numerous combinations of individual disc prosthesis elements available to suit the requirements of a particular patient. In various intervertebral prosthesis product systems, the upper plates, the lower plates, and the cores are provided to the sterile field of the surgical suite individually. Once the proper configuration of the upper plate, the lower plate, and the core has been determined, typically the surgical staff must acquire the proper upper plate, lower plate, and core from inventory.

The components of the prosthesis typically are then assembled for mounting with or loading into a prosthesis insertion tool, or assembled directly with the insertion tool, hi some systems, an assembly stand or jig is used for assembling the prosthesis components and loading the assembled prosthesis into an insertion tool. The selection and assembly process can be time consuming and awkward, potentially resulting in delays during the surgical proceeding. Handling of the components during assembly process can compromise the sterility of the prosthesis, and the use of additional handling equipment, such as an assembly stand or jig, can require further sterilization procedures, increase the complexity of the procedure, and clutter the surgical suite.

In some systems, an assortment of insertion tools are each configured for use with a single size or a limited range of sizes of the various prosthesis component combinations. Generally, the required size and configuration of the various prosthesis components will not be known until the surgical procedure has commenced. Thus, the surgeon will have to select the proper insertion tool during the procedure, following the determination of the proper sizes and configurations of the various prostheses components. The surgical staff therefore must disinfect and sterilize several insertion tools to have a full selection of the insertion tools at hand during the procedure. During the procedure, selection of the appropriate tool and confirmation of the selection will add to the duration and complexity of the surgical procedure. In various designs of insertion tools, however, the operative components of the insertion tool body are the same regardless of the prosthesis configuration, and only the tool's insertion adapter (for example, a head, holder, or other carrier of the assembled prosthesis) differs among the various insertion tools. Often, the differences among the various insertion adapters are dictated solely by the differences in sizes and configurations of the prosthesis components.

SUMMARY

In this context, one purpose of the present invention is to overcome the drawbacks of the prior art by proposing an intervertebral disc prosthesis delivery and insertion system which is easy to use and which can be provided in a stock which can be directly used during surgical procedures.

This purpose of the invention is reached by an intervertebral disc prosthesis delivery and insertion system comprising:
 (a) a demountable insertion tool body; and
 (b) plural intervertebral disc prosthesis insertion assemblies, each sterilized and packaged in sterile packaging to form a sterile pack and each comprising:
  (i) an insertion adapter having a coupler for the demountable insertion tool body and
  (ii) an intervertebral disc prosthesis releasably mounted to the insertion adapter.

According to another particular feature, the intervertebral disc prosthesis has a size and configuration specification.

According to another particular feature, the system further comprises an inventory storage space having storage locations for selected ones of the size and configuration specifications.

According to another particular feature, each sterile pack bears identifying information observable when the respective sterile pack is stored in the inventory storage space.

According to another particular feature, each storage location corresponds to one of the selected ones of the size and configuration specifications.

According to another particular feature, each of the intervertebral disc prostheses comprises:
 a first plate having a size and configuration selected from a set of first size and configuration specifications,
 a second plate having a size and configuration selected from a set of second size and configuration specifications, and
 a core having a size and configuration selected from a set of third size and configuration specifications.

According to another particular feature, the set of first size and configuration specifications is identical to the set of second size and configuration specifications.

According to another particular feature, one or more of the set of first size and configuration specifications, the set of second size and configuration specifications, and the set of third size and configuration specifications contains only one element.

According to another particular feature, the system further comprises an inventory storage space having storage locations for selected combinations of first size and configuration specifications, second size and configuration specifications, and third size and configuration specifications.

According to another particular feature, each primary sterile pack bears identifying information observable when the respective primary sterile pack is stored in the inventory storage space.

According to another particular feature, each storage location corresponds to one of the selected combinations of first size and configuration specifications, second size and configuration specifications, and third size and configuration specifications.

According to another particular feature, each storage location bears information observable when the location is empty, said information identifying the one of the selected combinations of first size and configuration specifications, second size and configuration specifications, and third size and configuration specifications to which such location corresponds.

Another purpose of the present invention is to overcome the drawbacks of the prior art by proposing Intervertebral Disc Prosthesis Insertion Assemblies which are easy to use and which can be provided in a stock which can be directly used during surgical procedures.

This purpose is reached by an intervertebral disc prosthesis insertion assembly comprising an insertion adapter having a coupler for a demountable insertion tool body and an intervertebral disc prosthesis releasably retained by the insertion adapter.

According to another particular feature, the insertion adapter and the intervertebral disc prosthesis are disposed in sterile packaging to form a sterile pack.

According to another particular feature, the insertion adapter has a surface complementary to and substantially fitting the intervertebral disc prosthesis.

According to another particular feature, the insertion adapter has at least one retainer that engages a recess and/or a post of the intervertebral disc prosthesis.

According to another particular feature, the retainer is a latch, and the recess is disposed on an edge of a plate of the intervertebral disc prosthesis.

According to another particular feature, the retainer is a dog, and the recess is disposed along a core of the intervertebral disc prosthesis.

According to another particular feature, the dog has a channel substantially matching the edge of a post of a plate of the intervertebral disc prosthesis.

Another purpose of the present invention is to overcome the drawbacks of the prior art by proposing packaged Intervertebral Disc Prosthesis Insertion Assemblies which are easy to use and which can be provided in a stock which can be directly used during surgical procedures.

This purpose is reached by a packaged intervertebral disc prosthesis insertion assembly comprising a sterile pack in which are disposed a sterile insertion adapter having a coupler for a detachable insertion tool body and components of a sterile intervertebral disc prosthesis.

According to another particular feature, the components of the intervertebral disc prosthesis are assembled and retained by the insertion adapter.

Another purpose of the present invention is to overcome the drawbacks of the prior art by proposing Intervertebral Disc Prosthesis Insertion Systems which are easy to use and which can be provided in a stock which can be directly used during surgical procedures.

This purpose is reached by an intervertebral disc prosthesis insertion system comprising:
 an insertion adapter having a coupler for a detachable insertion tool body; a detachable insertion tool body; and
 an intervertebral disc prosthesis releasably mounted to the insertion adapter.

According to another particular feature, the insertion adapter and the intervertebral disc prosthesis are disposed in sterile packaging to form a sterile pack.

According to another particular feature, the insertion tool body comprises an insertion actuator.

According to another particular feature, the insertion tool body comprises an insertion stop.

According to another particular feature, the insertion stop lock is adjustable.

According to another particular feature, the insertion tool body comprises an insertion stop lock.

Another purpose of the present invention is to overcome the drawbacks of the prior art by proposing methods for Intervertebral Disc Prosthesis Insertion which are easy to use and which can be provided in a stock which can be directly used during surgical procedures.

This purpose is reached a method of inserting an intervertebral disc prosthesis between adjacent elements of a spinal column, the method comprising the steps of:

providing an insertion adapter and an intervertebral disc prosthesis;
mounting the intervertebral disc prosthesis to the insertion adapter to form an insertion assembly;
providing an insertion tool body;
mounting the insertion assembly to the insertion tool body;
inserting the intervertebral disc prosthesis between adjacent elements of a spinal column; and
demounting the intervertebral disc prosthesis from the insertion assembly.

According to another particular feature, the method further comprises the step of demounting the insertion adapter from the insertion tool body and discarding the insertion adapter.

This purpose is also reached by a method of inserting an intervertebral disc prosthesis between adjacent elements of a spinal column, the method comprising the steps of:
providing an insertion adapter and components of an intervertebral disc prosthesis; assembling the components of the intervertebral disc prosthesis and the insertion adapter to form an insertion assembly; providing an insertion tool body;
assembling the insertion assembly and the insertion tool body; placing the intervertebral disc prosthesis between adjacent elements of a spinal column; and
removing the intervertebral disc prosthesis from the insertion assembly.

According to another particular feature, the step of providing an insertion adapter and components of an intervertebral disc prosthesis comprises the steps of:
packaging the components of the intervertebral disc prosthesis and the insertion adapter in sterile packaging to form a sterile pack; and then
transporting the sterile pack to a sterile field.

According to another particular feature, the method further comprises the steps of:
packaging the insertion assembly in sterile packaging to form a sterile pack;
and then
transporting the sterile pack to a sterile field.

This purpose is also reached by a method of aseptically delivering an intervertebral disc prosthesis insertion assembly to a sterile field, the method comprising the steps of:
providing sterile components of an intervertebral disc prosthesis and a sterile insertion adapter having a coupler for a detachable insertion tool body;
packaging the components of the intervertebral disc prosthesis and the insertion adapter into sterile packaging to form a primary sterile pack;
transporting the sterile pack containing the intervertebral disc prosthesis and the insertion adapter into a sterile field; and
removing the intervertebral disc prosthesis and the insertion adapter from the sterile pack within the sterile field.

According to another particular feature, the method further comprises, prior to the step of packaging, the step of assembling the components of the intervertebral disc prosthesis and the insertion adapter.

According to another particular feature, the method further comprises the step of packaging the primary sterile pack into a secondary sterile pack.

Another purpose of the present invention is to overcome the drawbacks of the prior art by proposing packaged Intervertebral Disc Prosthesis Insertion Assemblies which are easy to use and which can be provided in a stock which can be directly used during surgical procedures.

This purpose is reached by a packaged intervertebral disc prosthesis insertion assembly comprising a sterile pack in which are disposed a sterile insertion tool and sterile components of an intervertebral disc prosthesis.

According to another particular feature, the components of the intervertebral disc prosthesis are assembled with the sterile insertion tool.

Another purpose of the present invention is to overcome the drawbacks of the prior art by proposing Intervertebral Disc Prosthesis Insertion Systems which are easy to use and which can be provided in a stock which can be directly used during surgical procedures.

This purpose is reached by an intervertebral disc prosthesis delivery and insertion system comprising plural packaged intervertebral disc prosthesis insertion assemblies, each of the packaged intervertebral disc prosthesis insertion assemblies comprising a sterile insertion tool and sterile components of an intervertebral disc prosthesis packaged in sterile packaging to form a primary sterile pack.

According to another particular feature, each of the intervertebral disc prostheses has a size and configuration specification.

According to another particular feature, the system further comprises an inventory storage space having storage locations for selected ones of the size and configuration specifications.

According to another particular feature, each primary sterile pack bears identifying information observable when the respective primary sterile pack is stored in the inventory storage space.

According to another particular feature, each storage location corresponds to one of the selected ones of the size and configuration specifications.

In various embodiments, an intervertebral disc prosthesis is provided. The prosthesis may be provided with an insertion adapter, such as a head, holder, or other carrier of the prosthesis. The insertion adapter may be configured to retain the prosthesis and to engage an insertion tool body. In various embodiments, the prosthesis and the insertion holder are provided in a sterile pack, with the prosthesis components and the insertion holder sterilized and packaged in one or more types or layers of sterile packaging. In various embodiments, the prosthesis and an insertion tool are provided in a sterile pack, with the prosthesis components and the insertion holder sterilized and packaged in one or more types or layers of sterile packaging. Intervertebral disc prosthesis insertion assemblies, intervertebral disc prosthesis insertion systems, intervertebral disc prosthesis delivery and insertion systems, methods of inserting an intervertebral disc prosthesis between adjacent elements of a spinal column, methods of inserting an intervertebral disc prosthesis between adjacent elements of a spinal column, and methods of aseptically delivering an intervertebral disc prosthesis insertion assembly to a sterile field are also disclosed.

BRIEF DESCRIPTION OF THE SEVERAL VIEWS OF THE DRAWINGS

Other features and advantages of various embodiments and various aspects of the present invention will appear more clearly to those of skill in the art on reading the description that follows, with reference to the appended drawings in which.

DETAILED DESCRIPTION OF VARIOUS EMBODIMENTS

Figure 1:
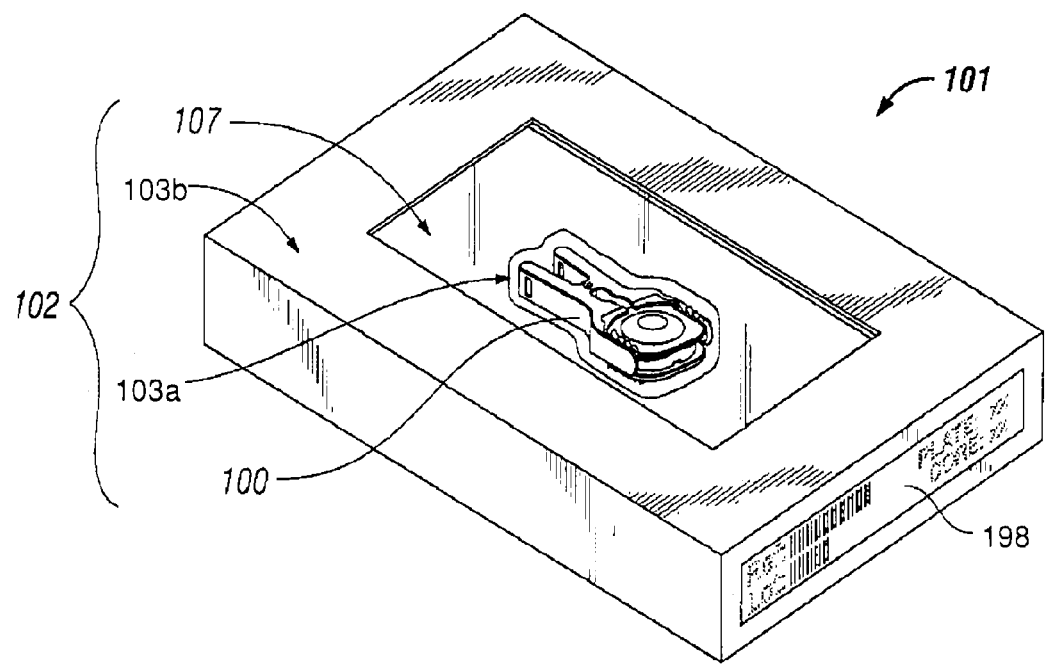
FIG. 1 depicts an embodiment of a sterile pack comprising a prosthesis insertion assembly.
Figure 2:
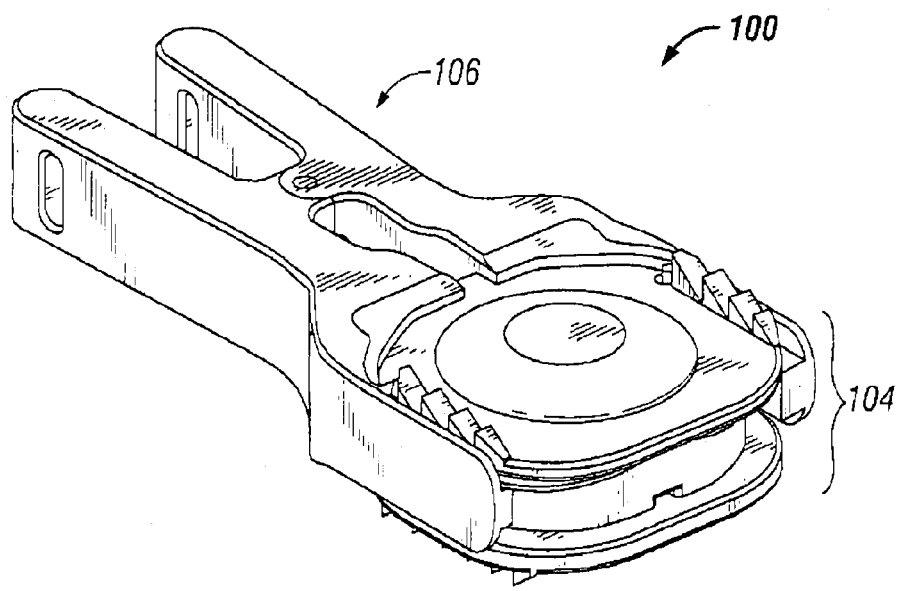
FIG. 2 depicts an embodiment of a prosthesis insertion assembly.

In several embodiments of the invention, the prosthesis insertion assembly is arranged so that it is possible that the prosthesis is never directly touched during the insertion procedure. This arrangement is particularly advantageous in that it limits or prevents the risks of contamination of the prosthesis during the insertion procedure. Various embodiments of a sterile package or sterile prosthesis insertion assembly are provided to facilitate the insertion of the prosthesis between adjacent vertebrae and so that the surgeon can use an assembly for the insertion of the prosthesis without having any direct contact with the prosthesis. FIG. 1 depicts one of many possible embodiment of a packaged intervertebral disc prosthesis insertion assembly (101). In this embodiment, a sterile insertion adapter (106) and sterile components of an intervertebral disc prosthesis (104) may be assembled together to form a sterile prosthesis insertion assembly (100) as shown in FIG. 2, which is disposed in primary, or inner, sterile packaging (103a) and in secondary, or outer, sterile packaging (103b) to form a sterile pack (102). The components of the intervertebral disc prosthesis (104) may be assembled with the insertion adapter (106) and provided to the sterile field of a surgical suite pre-configured and ready to use. It will be understood that the configurations of a primary (103a) and secondary (103b) packaging to form a sterile pack (102, 202) are arbitrary and that the invention can be used with other configurations of packaging, such as, for example, a sterile pack (102, 202) comprising only one layer, two layer (as in the above example when considering that the primary and secondary package are layers) or more than two layers, each layer possibly being different one of another. The various elements forming the assemblies explained below can be packed in such packaging, assembled or not, with a preference of at least all the component of the prosthesis being assembled, for example mounted to an adapter, for example held by an insertion tool. With such configurations, the sterile pack will be delivered to the sterile field for implantation onto a patient and the components of the prosthesis will not be touched during the insertion procedure, thus limiting the risks of contamination.

FIG. 2 depicts one of many potential embodiments of an insertion assembly (100). Various embodiments of the insertion assembly (100) may comprise an intervertebral disc prosthesis (104) and an insertion adapter (106), which holds the prosthesis (104) and couples with, mounts to, or otherwise joins or engages a detachable or demountable surgical tool body (130), for example as illustrated in FIG. 4, used in implanting the prosthesis (104). The prosthesis (104) can be of the type manufactured by LDR Medical, described herein or in the patents FR 2 824 261, FR 2 846 550, FR 2 865 629, FR 2 869 528, FR 2 879 436 (corresponding, respectively to applications WO 02/089701, WO 04/041129, WO 2005/074839, WO 2005/104996 and WO 2006/120505), or in applications FR 2 891 135 and FR 2 893 838 (corresponding, respectively to applications WO 2007/034310 and WO 2007063398), filed by the applicant of the present application (or corresponding US applications assigned to the assignee of the present application). Such prostheses can comprise, for example, at least a first plate, a second plate and a core mobile in rotation and/or in translation in relation to at least one of the plate, with arrangements for cooperation of the core and at least one of the plates, so as to limit or prevent the movements of the core in relation to at least one of the plates. The invention can also comprise a prosthesis of another type, for example as known from prior art and possibly including the various arrangements necessary for its use in the assembly as described below. In the embodiment of FIG. 4, a clip (126), for example as illustrated in FIG. 3, provides additional restraint to the components of prosthesis (104).

Figure 3:
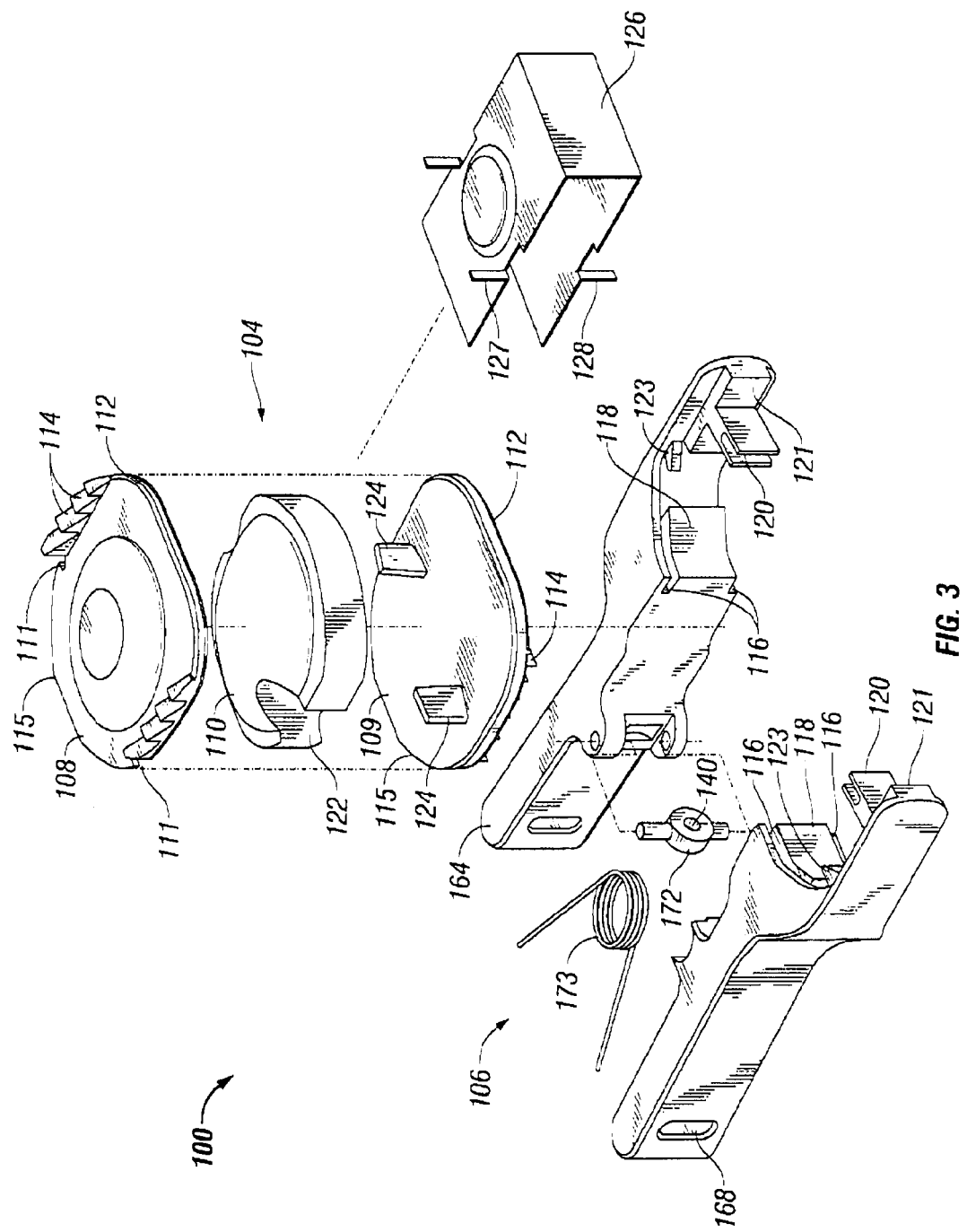
FIG. 3 depicts details of an embodiment of a prosthesis insertion assembly.
Figure 4:
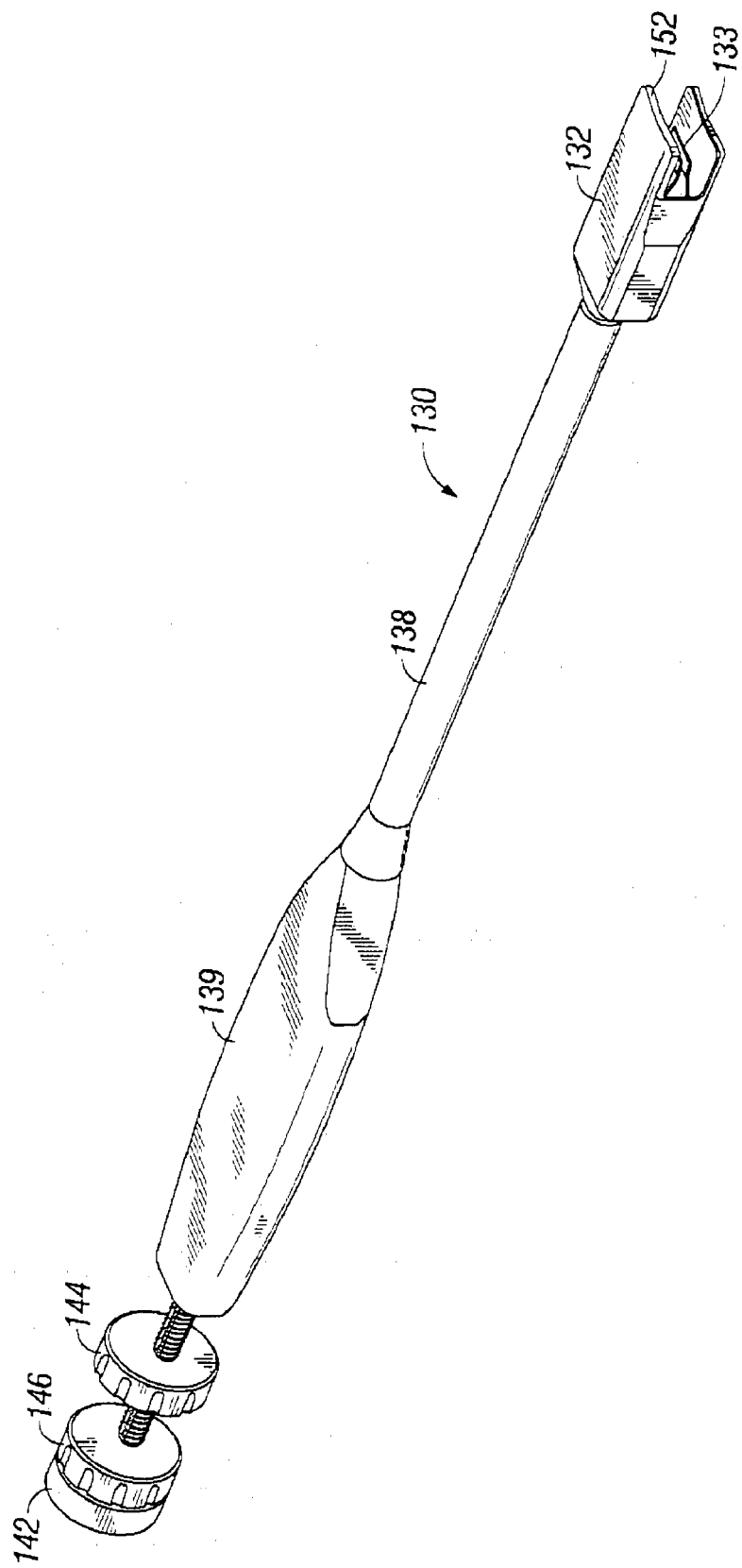
FIG. 4 depicts an embodiment of an insertion tool body.

FIG. 3 shows an exploded view of an embodiment of a prosthesis (104) and an insertion adapter (106). The prosthesis (104) in this embodiment comprises a first plate, such as upper plate (108), a second plate, such as lower plate (109), and a mobile core (110). The configurations of "upper" and "lower" plates generally are reversible, and the designation of the plates as "first plate" and "second plate" or as "upper plate" and "lower plate", of course, is purely arbitrary. The upper and lower plates (108, 109) preferably may be made of chromium, cobalt, and molybdenum, but other compositions may used. In various preferred embodiments, the core may be made of an ultrahigh molecular weight polyethylene but other compositions can be used. A titanium and hydroxyapatite plasma spray coating may optionally be applied to the vertebral contact surfaces of the upper and lower plates (108, 109) to encourage at least partial fusion with the adjacent vertebrae by bony ingrowth or other forms of adhesion. The prosthesis (104) in various embodiments may contain other features. For example, second plate (109) maybe configured with core-travel stops, for example posts (124) as illustrated, that limit the translational and rotational movement of core (110). In such embodiments, contact between the stops (124) and the recesses (122) along the perimeter of the core body may be configured to limit the translational and rotational movement of the core (110). The plates (108, 109) optionally may have angled edges (115) configured for complementary contact with optional angled contact surfaces (116) of the insertion adapter (106), the benefits of which are described in greater detail below.

Additional optional features of the prosthesis (104) may facilitate implantation of the prosthesis and its stability once implanted. For example, one or more of the edges of the prosthesis (104) that encounter the surfaces of the vertebrae (150) during prosthesis insertion may be beveled, for example edges (112) of the upper plate (108) and the lower plate (109), which may reduce the effort required to insert the prosthesis (104). Alternate embodiments may not contain this bevel at all, or may be beveled in only a few strategic locations around the perimeter of the plates (108, 109). Various embodiments also may have anchors (114) that, for example, may comprise notches or teeth disposed on either or both of the plates (108, 109) in the region of one or more edges of the prosthesis (104), or one or more anchors may be elsewhere along either or both of the vertebral contact surfaces of the plates (108, 109). The anchors (114) may be configured in such a way that they minimize the force required during the implantation of the prosthesis (104), while opposing subsequent movement of the prosthesis. After the prosthesis (104) is implanted, anchors (114) preferably stabilize the prosthesis (104) and oppose movement relative to the vertebrae (150) in multiple ways. For example, the anchors (114) may provide teeth opposing movement, primarily in the direction of removal, between the prosthesis (104) and the vertebrae (150), thus helping to keep the prosthesis (104) in place after implantation and during withdrawal of the insertion adapter (106). The surfaces of the plates (108, 109) also may have a porous biocompatible coating, for example as described above, that also allows adhesion of the osseous tissue and its fusion with the prosthesis. Once osseous tissue has adhered to the plates (108, 109) and grown around the anchors (114), a strong connection may be formed between each of the plates (108, 109) of the prosthesis (104) and the respective adjacent vertebra (150). In alternate embodiments, the porous, biocompatible coating may be replaced or supplemented with a porous, bioactive coating, which may stimulate the formation of osseous tissue, and/or with an antiseptic coating, which may deter or counteract infection at the surface of the implant.

After discectomy (whether complete or partial) and distraction of adjacent elements of a spinal column such as vertebrae (150), prosthesis implantation surgical procedures may involve measurements of intervertebral disc space. These measurements may be used to determine the dimensions and configurations of the upper plate (108), the lower plate (109), and the mobile core (110) to be implanted. In various embodiments, the prosthesis (104) generally may be configured to assist in the correction of various types of spinal disorders, including lordosis and kyphosis. Correction of lordosis or kyphosis may involve imposition of an angle, for example between 0 and 15 degrees, between the upper plate (108) and the lower plate (109) in the postero-anterior direction. The upper plate (108), the lower plate (109), or the core (110) may be configured to assist in imposing such an angle, for example as discussed in Patent FR 2 824 261 assigned to the assignee of the present application. Such angle can be imposed between the upper plate and the lower plate thanks to a core or nucleus having its upper and lower surface imposing an angle (one surface of the core being inclined with respect to the other) or by having at least one of the plate having its upper and lower surface imposing an angle (one surface of at least one of the plate being inclined with respect to the other surface of this plate). In addition, the plates (108, 109) and the core (110) generally have dimensions and configurations selected for the particular patient in which the prosthesis (104) will be implanted. Often, in practice the dimensions and configurations of the prosthesis (104) will not be known until well into the surgical procedure. Accordingly, for any particular patient the surgical staff will need an assortment of prosthesis insertion assembly configurations on hand.

Figure 22A:
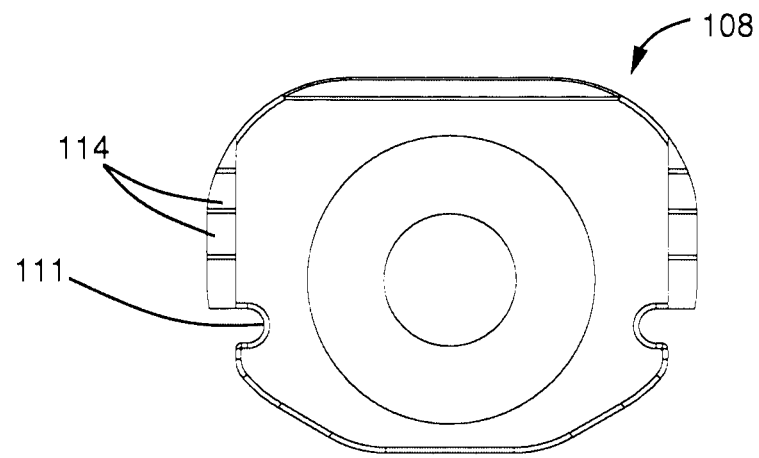
FIGS. 22A, 22B and 22C depict, respectively, an elevation view of a first plate of an intervertebral disc prosthesis, a side view of a second plate of an intervertebral disc prosthesis and an elevation view of the second plate of an intervertebral disc prosthesis, according to various embodiments.
Figure 22B:
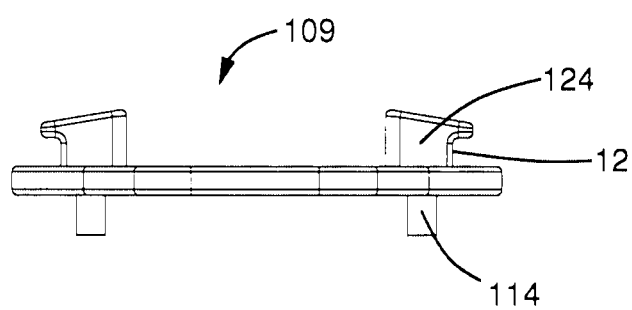
Figure 22C:
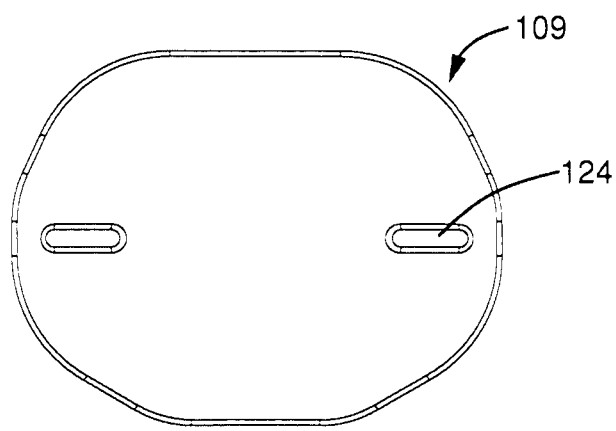

In various embodiments, the plates (108, 109) and core (110) of the prosthesis (104) may be retained by or releasably mounted to an insertion adapter (106). The insertion adapter (106) may be configured in many ways, such as a head, holder, or other carrier of an assembled prosthesis (104), for example. The insertion adapter (106) optionally may have jaws (121) that hold the prosthesis by grasping or pinching the lateral edges of the upper and lower plates of the prosthesis. The insertion adapter (106) may further comprise one or more optional retainers, such as mounting dogs (120). The dogs (120) may engage a respective recess (122) located in the mobile core (110) and contact or grasp a respective one of the posts (124) located on the lower plate (109). The dogs (120) may have surfaces configured to substantially match the spacing and/or configuration of the faces of the recesses (122). One or more of the dogs (120) may be equipped with a channel substantially matching the edge of one of the respective posts (124), to increase the effectiveness of the grasp on the lower plate (109). In addition, the insertion adapter (106) may optionally have additional retaining, grasping, or securing means, for example the illustrated latches (123) disposed on jaws (121), which may engage complementary retaining, grasping, or securing means, such as a receiver, recess, notch, etc., for example the recesses (111) disposed along opposite lateral edges of plate (108). For example, FIG. 22A depict an example of recess (111) enabling to an upper plate (108) to be held by an insertion adapter (106, not shown on this figure), for example thanks to latches (123), and FIG. 22B depict an example of a post (124) (shaft, jamb, stud or pillar) of a lower plate (109), enabling to this plate to be held and comprising a shoulder (12) intended to cooperate with dogs (120) of an insertion adapter (106), so as to maintain the prosthesis and avoid the prosthesis to fall when held by the adapter (106), for example of a type detailed later in reference to FIGS. 18(A to C). It will be understood, when reading the present description, that the various embodiments of the holder and adapter can be envisaged, with or without a supplementary clip (126) for holding the prosthesis.

The insertion adapter (106) in various embodiments also may comprise angled contact surfaces (116) configured for complementary contact with optional angled edges (115) of the prosthesis plates (108, 109). An optional shoulder (118) may be configured for complementary contact with the perimeter of the core (110). The combined height of the contact surfaces (116) and the shoulder (118) may preferably be substantially equal to the distance between the plates (108, 109) of an assembled prosthesis (104). The contact surfaces (116) and the shoulder (118) in various embodiments thus may combine to provide a surface of the insertion adapter (106) complementary to, and substantially fitting, the prosthesis (104) when assembled with, or mounted or attached to, the insertion adapter (106). A complementary fit between angled structures such as this may help stabilize the prosthesis (104) and push its components uniformly into the intervertebral disc space, preventing unwanted rotation or transverse movements of the prosthesis (104) or its components during insertion. Various embodiments may incorporate any or all of the structures discussed above, but may also have other attachment and support mechanisms. For example, some embodiments optionally may have additional mount points, such as in the upper plate (108), the lower plate (109), or both. Other alternative embodiments could have retainers such as pins or clips that fit into one or more cavities or recesses of various prosthesis components, or one or more of many other methods that could be used to grasp objects and allow for convenient release when desired.

The insertion adapter (106) in various embodiments may have actuator means for releasing the intervertebral this prosthesis (104). In various embodiments, the actuator may be configured as spring-loaded arms, tangs, shanks, or other actuating means (164) articulable about articulating means such as a hinge pin (172). Alternatively, the insertion adapter (106) may have an integral hinge portion about which the arms, tangs, shanks, or other actuating means (164) articulate, for example comprising a flexible material such as plastic or rubber or stress/strain relief features such as cuts or voids.

In some embodiments of the invention, the insertion adapter (106) can comprise a body split in at least two parts (164), complementary one with another and assembled so as to hold at least part of the prosthesis (104), at least at an end of the adapter (106) comprising dogs (120) or latches (123). These dogs or latches (120, 123) can, in some embodiments, be formed by branches prolonging a lateral surface of each of the parts (164) of the adapter's body. The term "dogs" shouldn't be construed restrictively since the arrangement can be formed by branches having a shape adapted to hold the prosthesis at an end of the branch, as detailed below. Preferably, the adapter (106), in these embodiments, will be split along its longitudinal axis (i.e., the axis of insertion of the prosthesis) so that the 2 parts of its body surround and hold the prosthesis on the lateral faces of the latter. Thus, in these embodiments, the actuating means (164) of the adapter (106) are formed by the assembly of the 2 parts of the body, for example thanks to a pin (165a) penetrating in a channel (165e) or hole, such as a drilling for example, passing through, at least partially, each of the parts (264) of the body of the insertion adapter (106). FIGS. 18(A to C), 19(A and B), 20(A to C), 21(A and B), 23(A to C) and 24(A and B), show several, illustrative but not limitative, examples of the possible embodiments and FIGS. 25(A and B) and 26(A to D) show examples of embodiments of a sterile insertion tool (131), particularly adapted to these embodiments of the insertion adapter (106). In these embodiments, actuating the insertion adapter (106) for releasing the prosthesis (104) will be performed by withdrawing the pin (165a) and by disassembling the two parts (164) of the body of the insertion adapter (106) forming the actuating means (164), as detailed hereafter. These embodiments of the insertion adapter (106) can also be pre-assembled with the prosthesis (104) in a sterile package, eventually with the sterile insertion tool (131).

Figure 18A:
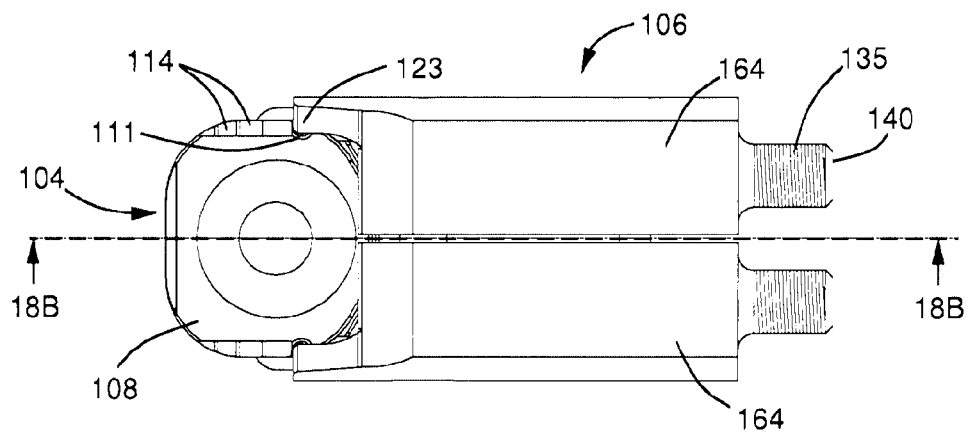
FIGS. 18A, 18B and 18C depict, respectively, an elevation view, a cross section view along cut plane (18B-18B) of FIG. 18A and a cross section view along cut plane (18C-18C) of FIG. 18B, of an embodiment of a prosthesis insertion assembly.
Figure 18B:
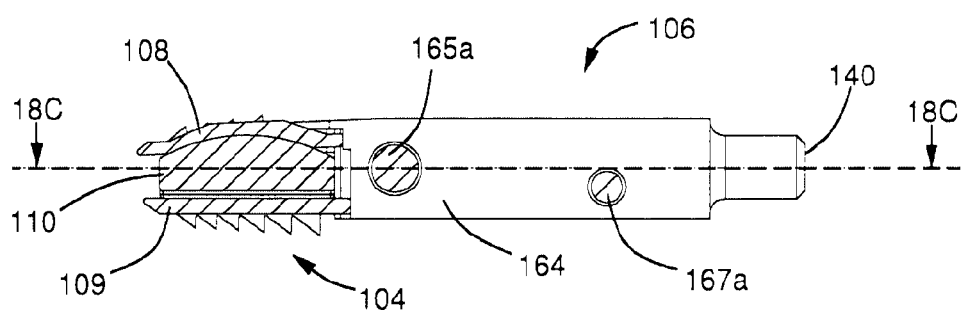
Figure 18C:
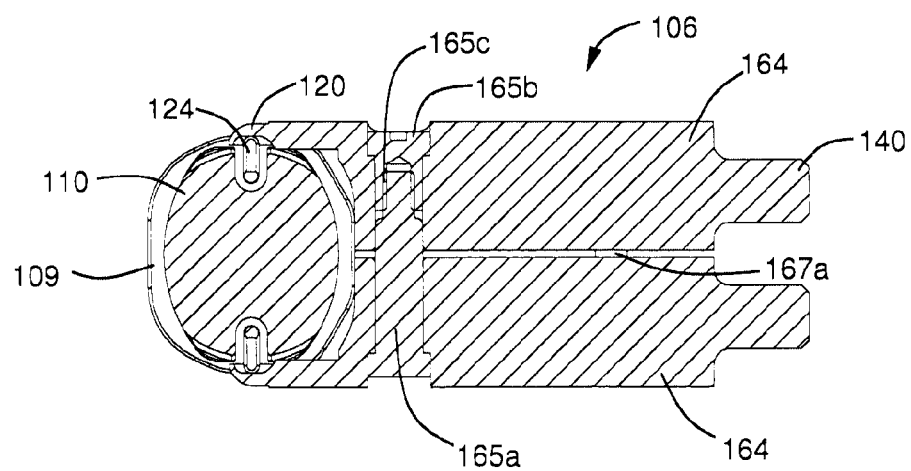
Figure 19A:
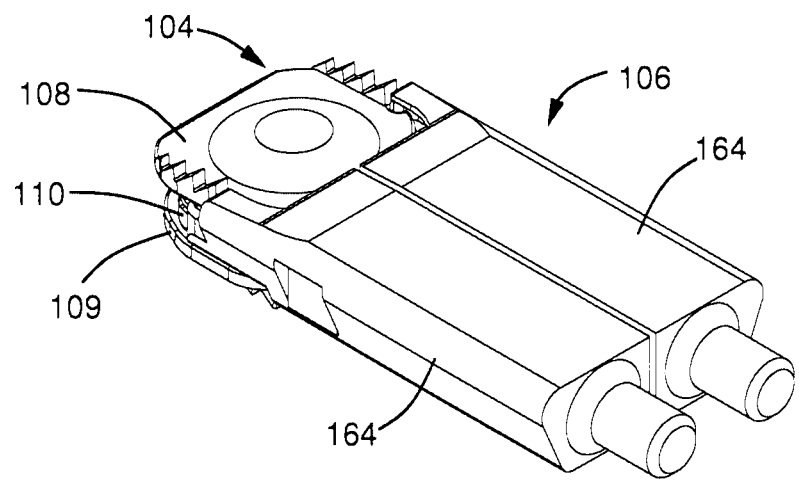
FIGS. 19A and 19B depict perspective views of an embodiment of a prosthesis insertion assembly, respectively assembled and disassembled.
Figure 19B:
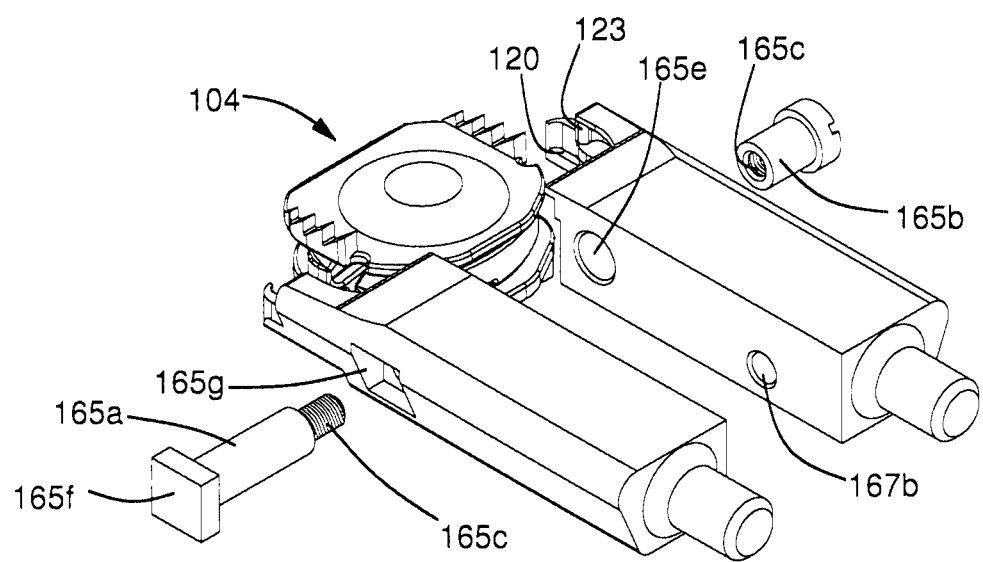

FIG. 18A show an embodiment of the insertion adapter (106) holding a prosthesis (104) in particular thanks to the cooperation between the latches (123) of the adapter and the recesses (111) of the upper plate (108) of the prosthesis (104), forming a mechanism for locking the prosthesis (104) on the adapter (106). The two parts (164) of the body of the adapter (106) have a substantially parallelepiped shape in this example shown on FIGS. 18(A to C), except at the end equipped with the dogs and latches for holding the prosthesis. Thus, the two parts (164) of the body, split along the longitudinal axis of the body, are assembled around the prosthesis and cooperate, in this example, through a substantially flat surface. The two parts (164) of the body of the adapter (106) are equipped with a coupler (140) enabling the adapter (106) to be mounted on an insertion tool (131, FIGS. 25A and 25B, for example). It should be noted that several variants of implementation comprising only one coupler on only one of the two parts of the body of the adapter can be envisaged. In the example shown, this coupler (140) comprises a shank intended to cooperate an actuator (136, FIG. 25B), such as a rod for example, provided with a threaded hole (134) for its screwing onto the coupler (140). It will be noted that the configuration of the shank (threaded rod) of the coupler (140) and the threaded hole (134, FIG. 26B) of the actuator (136) of the insertion tool (131) can of course be inversed or be replaced by other arrangements for coupling (holding, fixing) the adapter (106) and the insertion tool (131). Thus, for example, the coupler of the adapter can comprise a threaded hole (140) cooperating with a threaded end (134) of the actuator (136) of the insertion tool. In other embodiments, the coupler (140) can comprise a rod provided with a flat (165d) intended to cooperate with a duct comprising a shoulder, at an end of the actuator (136, FIG. 25B). In other embodiments, the coupler (140) can comprise a rod, threaded and comprising a flat (165d), so that the adapter (106) and/or the pin (165a) (in the case where it is the pin (165a) which holds the coupler (140) as detailed hereafter) can be manipulated both by a tool comprising a shoulder cooperating with the flat and by a tool comprising a threaded hole. Furthermore, other embodiments envisaged comprise a coupler having a threaded hole at the bottom of which a shoulder is arranged, such coupler thus being capable to cooperate both with a threaded end (134) of an actuator (136, FIG. 25B) and with a tool comprising a rod having a flat at one end. FIG. 18B show a cross section of such embodiment, with the angled edges (115) of the plates (108, 109) of the prosthesis abutting the angled surfaces or edges of the adapter (106). In some embodiments (not shown), the adapter (106) also comprises a shoulder or a surface for contact with the core (110) for maintaining the various elements (108, 109, 110) of the prosthesis in a position suited for the insertion between vertebrae. As particularly visible on FIG. 18C, the assembly of the two parts (164) of the body of the adapter (106) is performed in this example by at least one pin (165a) transversally passing through the adapter (106), from side to side, in the horizontal plane. In this example, the pin (165a) is provided with a threaded end (165c) enabling its screwing in a threaded hole of a swivel (or any other arrangement for assembling). The screwing of the pin (165a) and the swivel (165b) allows maintaining together the two parts (164) of the body of the adapter which maintain (hold, surround) the elements of the prosthesis, in particular thanks to the dogs (120) cooperating with the post (124) of the lower plate (109) of the prosthesis and eventually to the latches (or dogs) (123) cooperating with the recesses (11) mentioned previously. In the example depicted in FIG. 18C, the assembly of the two parts (164) of the adapter's (106) body is strengthened by a rod (167a) protruding from one of the two parts (164) and penetrating in a hole (167b, FIG. 19b) of the other part. However, this strengthening (167a, 167b) of the assembly is not critical and some embodiments only comprise the pin (165a). As particularly visible on FIG. 19B, the pin (165a) can comprise, in some embodiments, a stop (165f) cooperating with a housing (165g) of complementary shape, arranged in one of the two parts (164) of the adapter's (106) body, so as to oppose to the rotation of the pin (165a) during the screwing of the swivel (165b). Thus, the adapter's assembly can simply be performed by inserting the pin (165a) into a hole (165e) passing through the two parts (164) of the body and by the screwing of the threaded hole (165c) of the swivel (165b) onto the threaded end (165c) of the pin (165a). It should be noted that the term "swivel" is used herein to designate an element which can be screwed on a threaded rod but any similar structure can be used, for example the one shown in FIG. 19B and comprising a slit allowing the screwing with a screwdriver. Furthermore, instead of a swivel, a threaded hole disposed directly in one of the two parts (164) allows the screwing of a threaded pin (165a) without requiring other structures. Similarly, the configuration of the threadings can be inversed or replaced by any other arrangement for fixing the pin. It should be noted that, in the example shown on FIG. 19B, the dogs (123, 120) intended to maintain the plates are provided with a shoulder forming an horizontal surface supporting each plate, so that the prosthesis is maintained without requiring too much pressure on the recesses (111) and posts (124) of the plates.

Figure 20A:
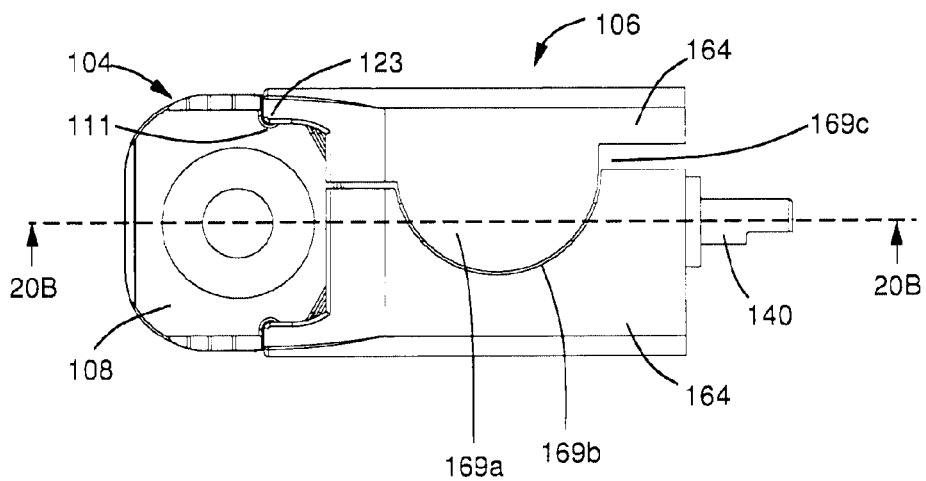
FIGS. 20A, 20B and 20C depict, respectively, an elevation view, a cross section view along cut plane (20B-20B) of FIG. 20A and a cross section view along cut plane (20C-20C) of FIG. 20B, of an embodiment of a prosthesis insertion assembly.
Figure 20B:
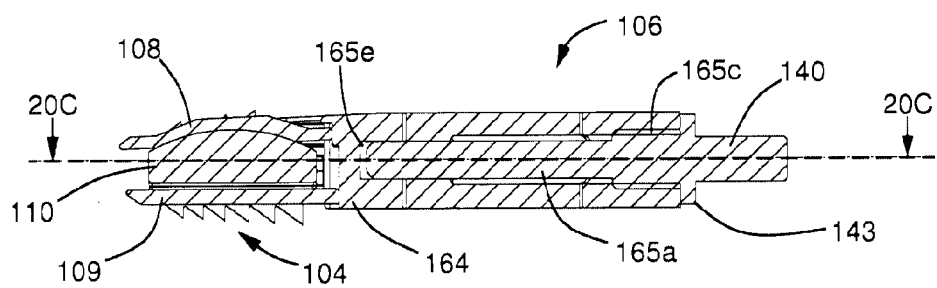
Figure 20C:
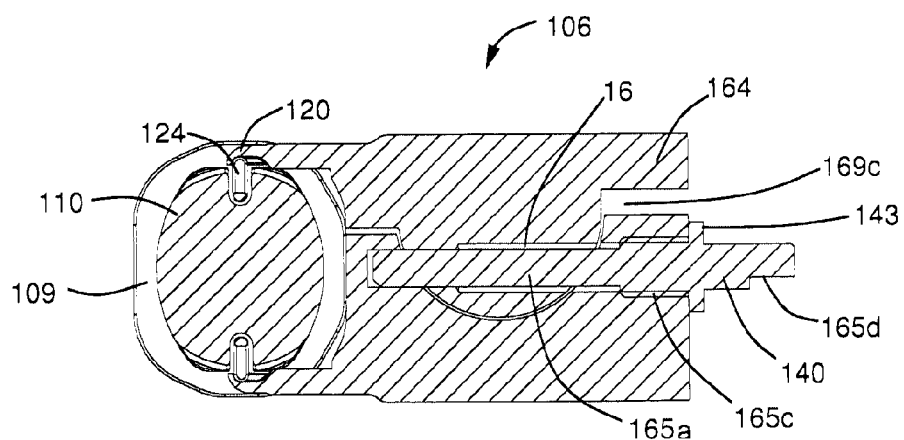
Figure 21A:
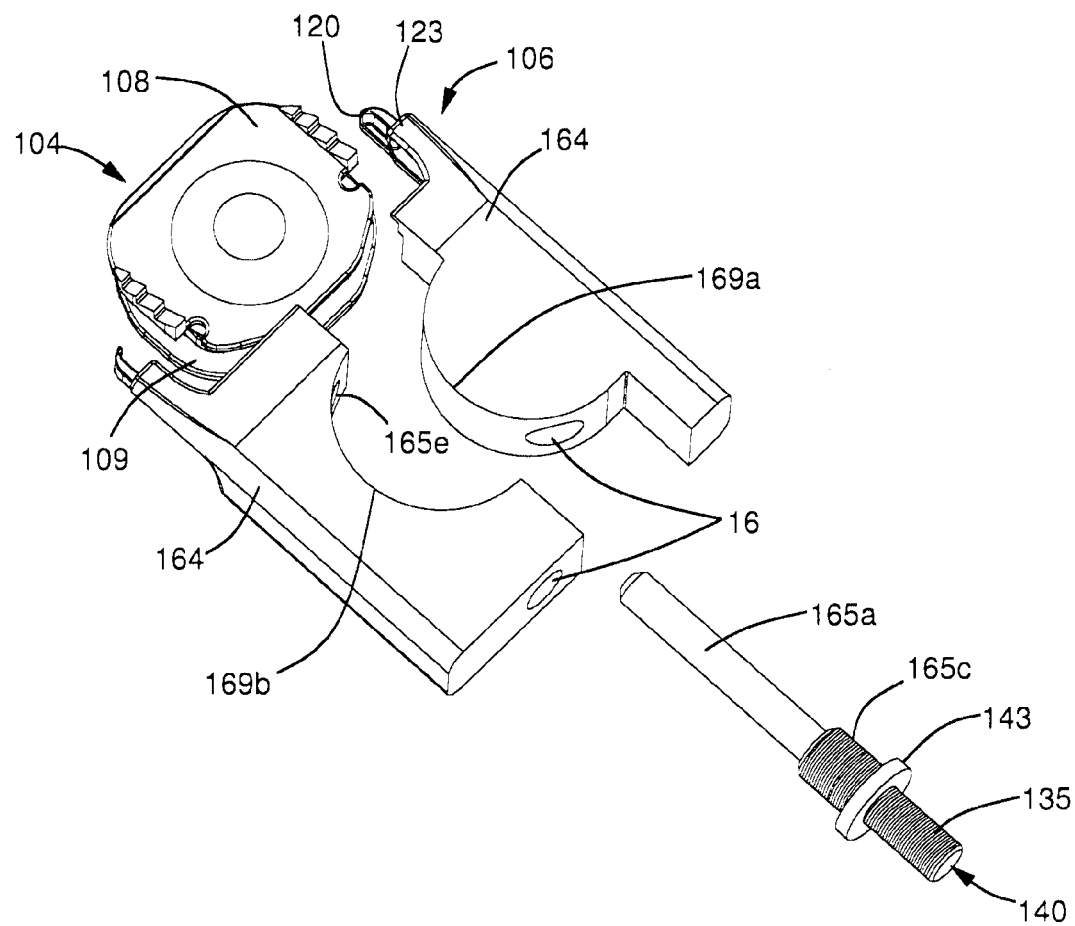
FIGS. 21A and 21B depict perspective views of, respectively, an embodiment of a disassembled prosthesis insertion assembly and an embodiment of an insertion adapter.
Figure 21B:
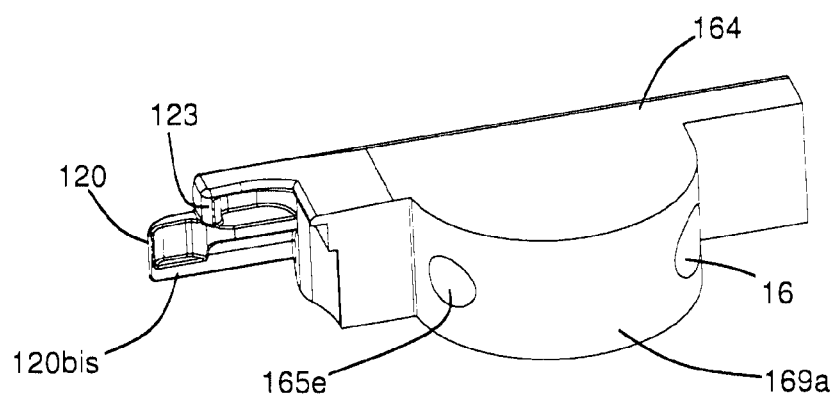

In some embodiments, an example of which is depicted in FIG. 20A, the two parts (164) of the adapter's (106) body cooperate together through curved surfaces: one part has a portion (169a) comprising a convex surface and the other has a portion (169b) comprising a concave surface, complementary to the convex surface. Thus, a first one of the two parts (164) forms a female part (169b) and the second one (164) forms a male part (169a) having a portion fitting into the female part (169b). In the example shown on FIG. 19A, the adapter (106) is at least partially crossed by a duct (or channel) (165e), such as a drilling for example, performed at the level of the male (169a) and female (169b) portions of the two parts of the body. Thus, a pin (165a) inserted in this duct (165e) enables assembling and maintaining together the two parts (164) of the adapter's body. In these embodiments, the duct (165e) and the pin (165a) are oriented along the longitudinal axis of the adapter (106). As particularly visible on FIGS. 20B and 20C, a threading (165c) on at least a portion of the pin (165a) can cooperate with a threading in the duct (165e). In this example, the pin also comprises a stop, for example such as a collar or skirt (143), for limiting the screwing of the pin. In some embodiments such as shown on FIGS. 20A to 20C, the male (169a) and female (169b) portions of the two parts (164) of the body are arranged so that a space (169c) is preserved between the two parts, at least at the end opposite the end holding the prosthesis. This space enables, when the pin (165a) is withdrawn from the duct (165e), that a pressure exerted on the lateral surfaces of the two parts (164), at the level of the end opposite the one holding the prosthesis, induces a rotation of the two part one in relation to the other, thanks to the complementarity of their respective curved surfaces and enables to free the prosthesis, in a manner similar to a clip. Furthermore, the duct (106e) can comprise an enlarged portion (16), so as to facilitate the insertion and withdrawal of the pin. The pin (165a) can, as shown on FIGS. 20(A to C), comprise a coupler (140) for the insertion tool (131). In this example shown, the coupler (140) comprises a flat (165d) intended to cooperate with a hole comprising a complementary shoulder, performed a one end of the actuator (136, FIG. 25B). Other configurations of the coupler (140) can of course be envisaged. For example, as particularly visible on FIG. 21A, the coupler (140) can consist of a stud or rod comprising a threading (135) on at least a portion and the pin (165a) can comprise a threading (165c) which screwing in the adapter is limited by a stop (143) such as a collar. In a particularly advantageous variant, the thread pitch of the threading (165c) of the pin (165a) and the thread pitch of the threading (135) of the coupler (140) are inversed, so that the screwing of the insertion tool (131) on the coupler (140) enables, when the tool stops on the collar (143), an unscrewing o the pin (165a) without requiring the surgeon to change the screw direction. FIG. 21B shows a detail of a part (164) of the adapter's body and, in particular, a shoulder (120bis) on dog (120) intended to hold the lower plate (109) of the prosthesis (104). This shoulder is arranged for efficiently maintaining the post (124) of the lower plate (109), which also comprises a complementary shoulder (12), as particularly visible on FIG. 22B. Similarly, FIG. 21B shows a dog (123) comprising a shoulder or a support surface for maintaining the upper plate (108).

Figure 23A:
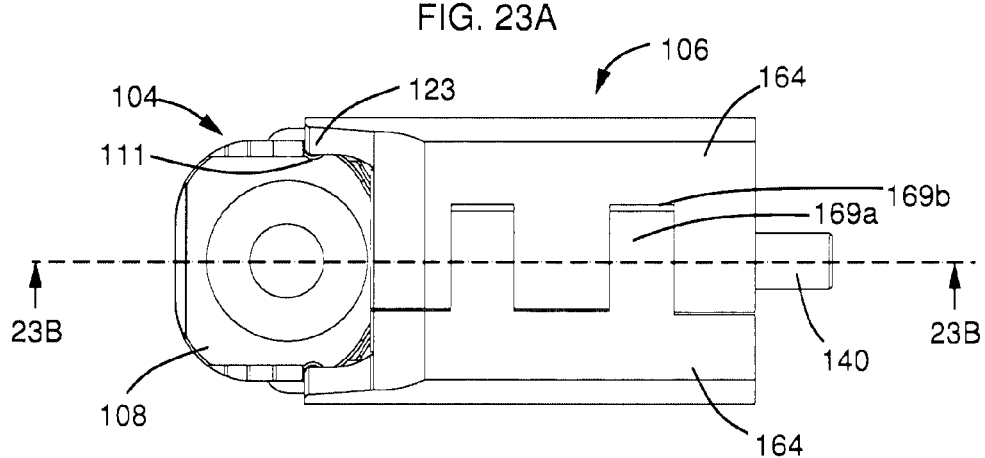
FIGS. 23A, 23B and 23C depict, respectively, an elevation view, a cross section view along cut plane (23B-23B) of FIG. 23A and a cross section view along cut plane (23C-23C) of FIG. 23B, of an embodiment of a prosthesis insertion assembly.
Figure 23B:
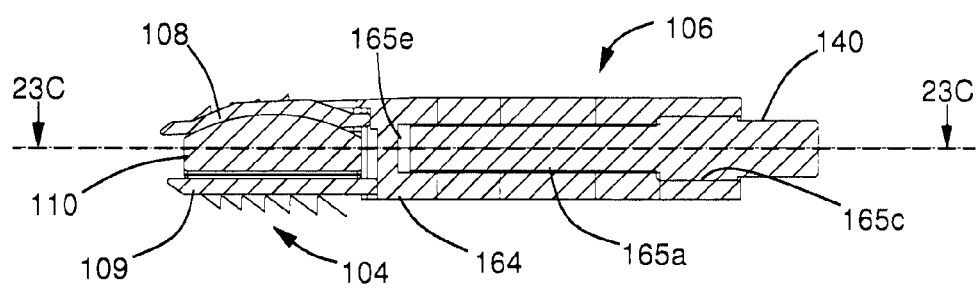
Figure 23C:
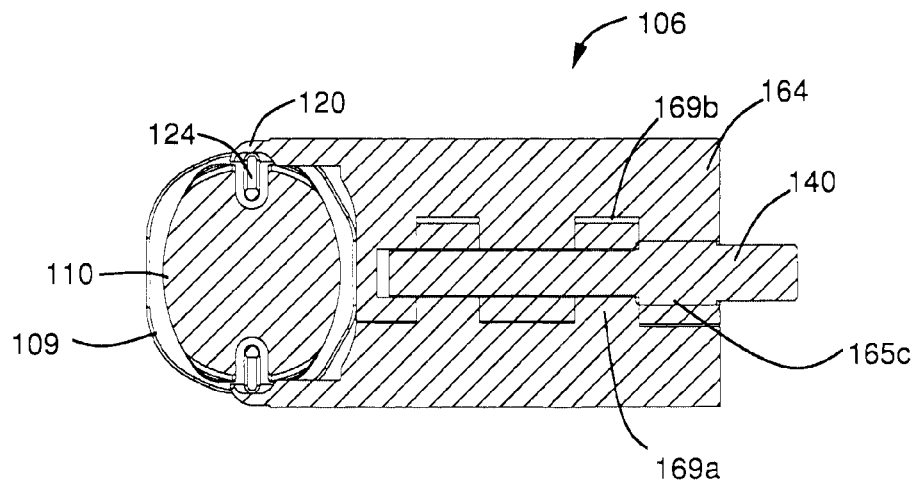
Figure 24A:
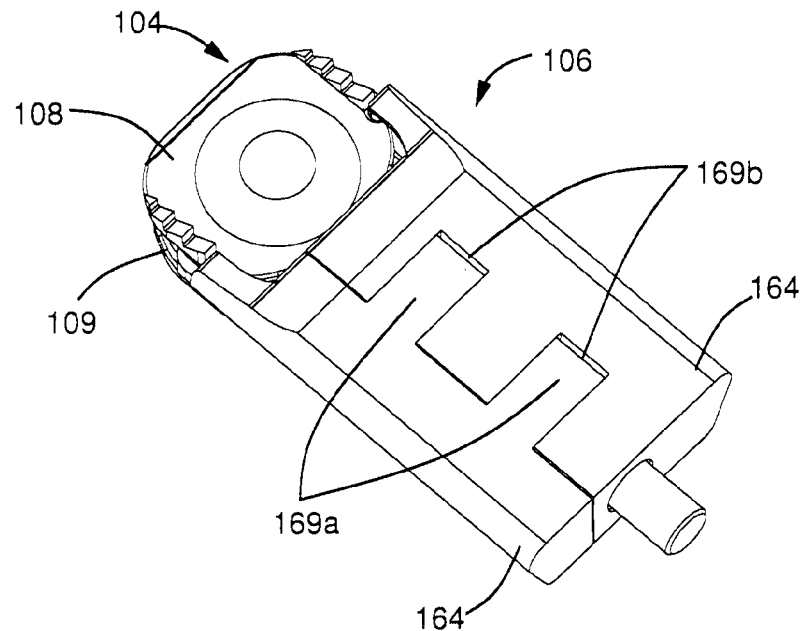
FIGS. 24A and 24B depict perspective views of an embodiment of a prosthesis insertion assembly, respectively assembled and disassembled.
Figure 24B:
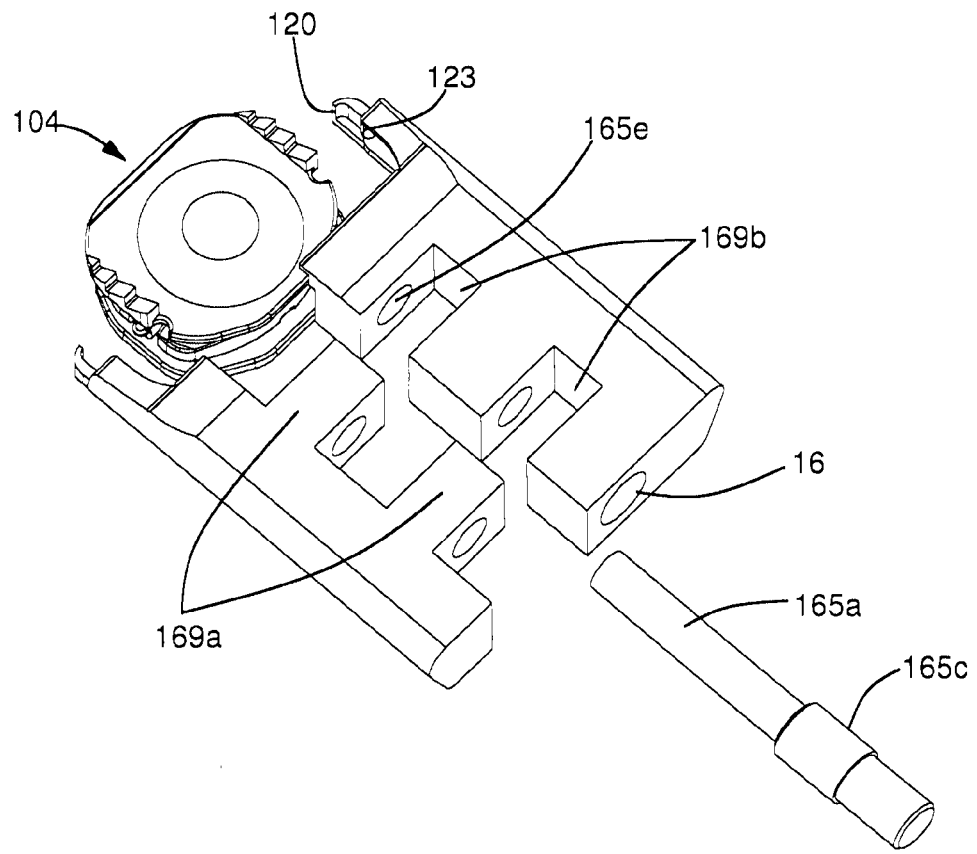

FIGS. 23A, 23B and 23C show another embodiment of the insertion adapter (106) split in two complementary parts (164). In this type of embodiments, a first one of the parts comprises at least one male portion (169a) and the second one comprises at least one female portion (169b) complementary to the male portion of the first part. In the example shown, two male portions having a substantially square or rectangular section cooperate with two female portions having a complementary shape. It will be understood, when appreciating the disclosure of this embodiment and the previous one, that the invention allows several embodiments of the male and female portions and that their number can vary. FIGS. 24A and 24 show the assembly/disassembly of the insertion adapter (106), by comparison, respectively, of an assembled view and a disassembled view of these embodiments. The assembly in this example is performed by bringing together the two parts (164) of the body and introducing the pin (165a) in the duct (165e). Similarly, the disassembly is performed by withdrawal of the pin and spreading of the two parts (164) apart.

Those of skill in the art, following appreciation of this disclosure, will recognize that many other structural configurations may be devised for the insertion adapter (106) to grasp the intervertebral disc prosthesis (104) and release the intervertebral this prosthesis (104) when inserted in an intervertebral disc space. Furthermore, the various embodiments and examples illustrated herein can be combined together, unless expressly mentioned herein or unless they are incompatible.

Some embodiments of the prosthesis insertion assembly (100) optionally may have a clip (126) that wraps around the assembled prosthesis (104) and holds the plates (108, 109) to the core (110). Retaining means such as the clip (126) augment the insertion adapter (106) in maintaining assembly of the prosthesis (104) during transport and/or during mounting, attaching, or assembling the insertion adapter (106) to or with the insertion tool body (130). Optionally, clip (126) may have one or more arrangement for removal (or removal means) to facilitate removal of the clip when the prosthesis insertion assembly (100) is assembled with, or mounted or attached to, an insertion tool body (130). These arrangements for removal can be such as tabs (127, 128) on the upper and lower surfaces (respectively) of the clip (126), as discussed further below.

In some preferred embodiments, the components of the intervertebral disc prosthesis (104) and the insertion adapter (106) may be sterilized using gamma radiation. Following sterilization, the components maybe packaged in primary sterile packaging (103a) to form a sterile pack (102), preferably with the components of the intervertebral disc prosthesis (104) and the insertion adapter (106) assembled as an insertion assembly (100), although packaging disassembled components of the intervertebral disc prosthesis (104) and the insertion adapter (106) is within the scope of this invention. In various preferred embodiments, the components of the intervertebral disc prosthesis (104) and the insertion adapter (106) that are packaged in primary sterile packaging (103a), whether assembled or disassembled, may be further packaged in a box or other container and enclosed in secondary sterile packaging (103b) to form a sterile pack (102). The sterile packaging (103a, 103b) may comprise bubble packaging, blister packaging, shrink wrapping, or other packaging configuration known to be suitable for maintaining the sterility of a medical implant. Sterile packaging (103a, 103b) in some embodiments preferably may have an oxygen absorbing packet, for example to reduce the potential for oxidative degradation of a polyethylene core (110) or other components. In preferred embodiments, the sterile pack (102) preferably may be made ready for delivery or transport to a sterile field of a surgical suite, directly or through a distributor.

Sterile packs (102) of insertion assemblies (100) preferably bear identifying information. For example, various embodiments optionally have a package label (198) with identifying information (180). The identifying information may include a use-before-date, the lot number and reference or serial number for the insertion assembly (100) or its components, a sterilization control label, and/or size and configuration information for the plates (108, 109) and the core (110). Preferably, the packaging label allows complete traceability of insertion assembly (100) from initial manufacturing through final implantation and service in a particular patient. In some embodiments, the sterile pack (102, 202) can comprise at least a transparent wall (107) enabling to see the insertion assembly (100, 101, 105) from outside the pack (102, 202).

Various embodiments described herein provide a surgical staff with an assortment or other inventory of pre-sterilized, pre-configured, and pre-assembled insertion assemblies (100). Optionally, a packaged intervertebral disc prosthesis insertion assembly may be provided with the intervertebral disc prosthesis (104) disassembled, along with an insertion adapter (106) preconfigured for use with the intervertebral disc prosthesis (104) following its assembly. In such embodiments, the components of the intervertebral disc prosthesis (104) typically would be assembled with the insertion adapter (106) in the sterile field to form an insertion assembly (100).

During a surgical procedure in various embodiments, the surgeon determines the appropriate dimensions and configurations of prosthesis (104). Measurements of the intervertebral disc space may, for example, be used in such a determination. Preferably, the surgical team may obtain the appropriate prosthesis insertion assembly (100) within the sterile field of the surgical suite from an inventory of prosthesis insertion assemblies (100).

In various disclosed embodiments such as shown in FIG. 4, whether providing the intervertebral disc prosthesis (104) assembled or disassembled, the prosthesis insertion assembly (100) may be configured for use with a detachable or demountable tool body (130), which may be used during the surgical procedure to implant the prosthesis (104) in the intervertebral disc space. The prosthesis insertion assembly (100) and the insertion tool body (130) preferably may be arranged or assembled for use, for example by attaching or mounting the prosthesis insertion assembly (100) to an insertion tool body (130), within the sterile field of a surgical suite.

Figure 5A:
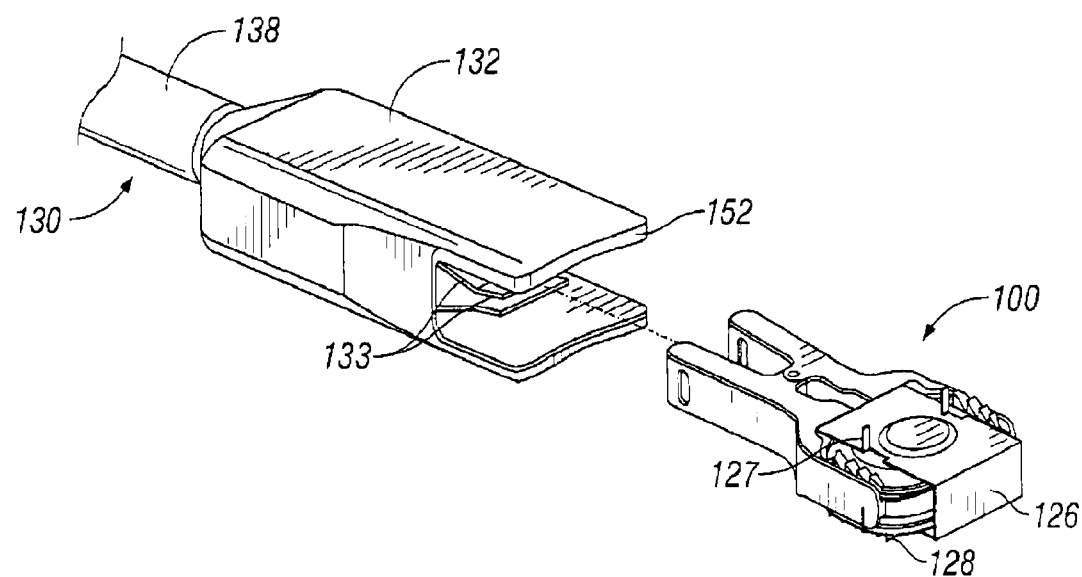
FIGS. 5A and 5b depict components of an embodiment of an insertion tool body and a prosthesis insertion assembly.
Figure 5B:
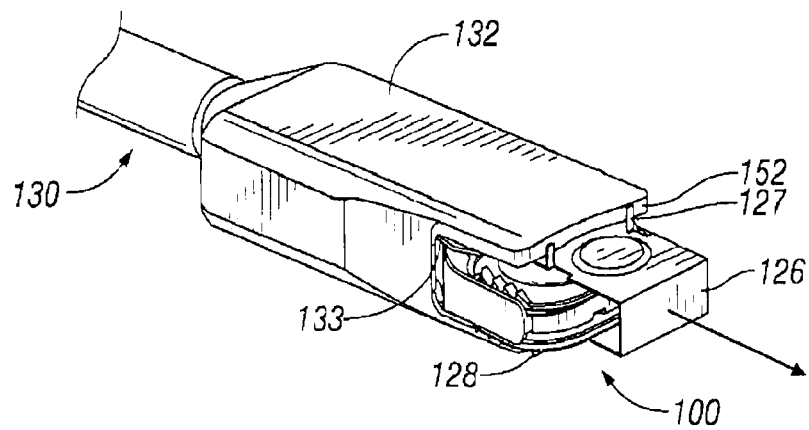

After removal from the sterile pack (102), the insertion assembly (100) and a detachable or demountable insertion tool body (130) are assembled. For the embodiments shown in FIGS. 5A and 5B, the prosthesis insertion assembly (100) may be lined up with a support (132), such as the illustrated housing for example, arranged to receive and support the prosthesis insertion assembly (100) during the implantation procedure. Preferably, the insertion tool body (130) may be adapted for use with all, or at least a wide assortment, of the various dimensions and configurations of intervertebral disc prostheses (104) available. There may be a wide variance in the heights of the various prostheses (104) in some embodiments of intervertebral disc prosthesis delivery and insertion systems. The support (132) optionally may be equipped with one or more retainers, for example the tongues (133) illustrated, to retain the prosthesis components in assembly. Other embodiments that deploy such retainers may use structures such as clips, pawls, springs, or other biasing components. Retainers such as tongues (133) may help center and support a wide variety of prosthesis dimensions and configurations with respect to support (132).

Figure 6A:
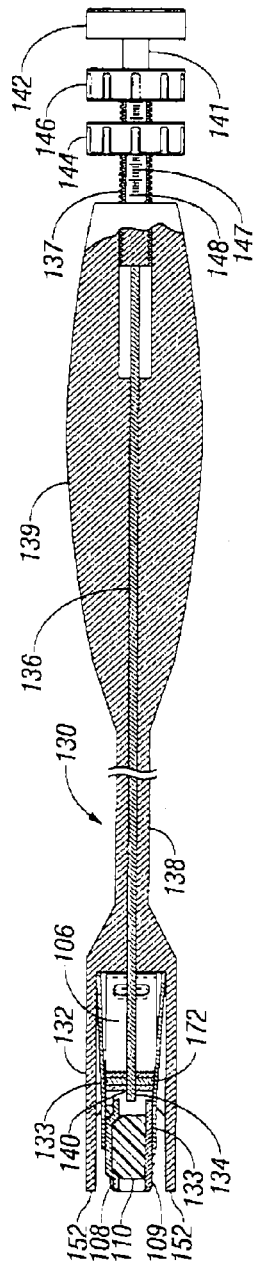
FIGS. 6A, 6B, and 6C depict various views of an embodiment of an insertion tool body.
Figure 6B:
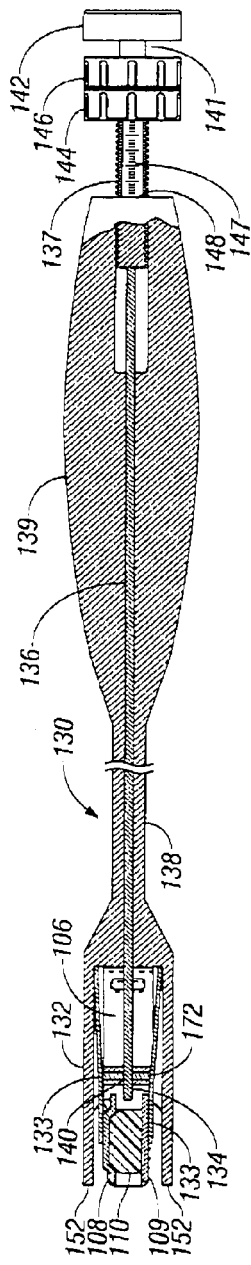
Figure 6C:
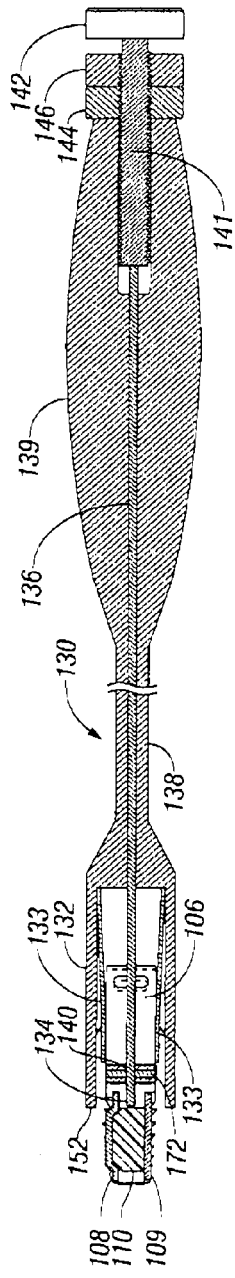

After appreciating the present disclosure, those of skill in the art will readily recognize numerous alternative means of mounting, coupling, assembling, attaching, or otherwise engaging a prosthesis insertion assembly (100) and an insertion tool body (130). For example, the insertion tool body (130) may be equipped with an actuator (136), such as a rod, shaft, cable, or other transmission or control structure, for example as illustrated in FIGS. 6A, 6B, and 6C. The actuator (136) in various embodiments may have engagement means, for example the illustrated threaded end (134) of the rod (136), to engage or connect with a coupler (140), for example the threaded hole illustrated in FIG. 3, of the insertion adapter (106). Once so engaged, the rod (136) may hold and push the insertion adapter (106) during the implantation procedure.

The prosthesis insertion assembly (100) optionally may be attached or mounted to the insertion tool body (130) by engagement of the threaded end (134) with threaded hole (140). The insertion assembly (100) may be disposed by hand at least partially within support (132), at least to the point where the insertion assembly (100) engages the threaded end (134). The insertion assembly (100) may be further disposed by hand fully within support (132), causing the threaded end (134) to recess into the member (138) of the insertion tool body (130). At this point, the threaded end (134) may be rotated in threaded hole (140) until appropriate engagement of the threads is achieved and the prosthesis insertion assembly (100) is firmly retained in support (132). Alternatively, the threaded end (134) may, upon initial engagement with threaded hole (140), be rotated in threaded hole (140) until the prosthesis insertion assembly (100) is drawn fully within and retained in support (132). Regardless of how the prosthesis insertion assembly (100) is disposed into support (132), tabs (127, 128) on the respective upper and lower surfaces clip (126) may be configured to contact leading edges (152) of support (132), respectively, well before the insertion assembly (100) is seated in the insertion assembly (100), causing the clip (126) to detach from the prosthesis (104) as the insertion assembly (100) is further moved into support (132), for example as depicted in FIG. 5.

Figure 25A:
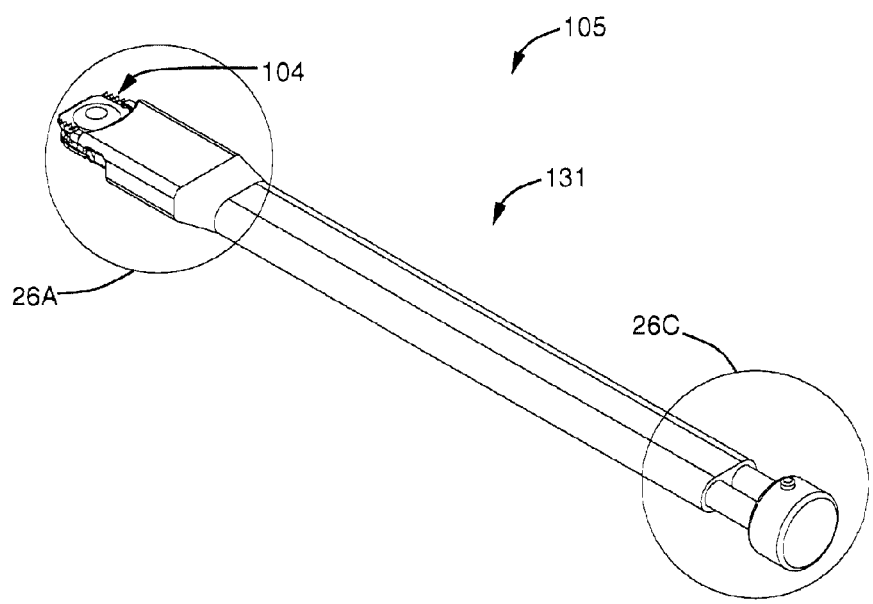
FIGS. 25A and 25B depict perspective views of an embodiment of a prosthesis insertion assembly, respectively assembled and disassembled.
Figure 25B:
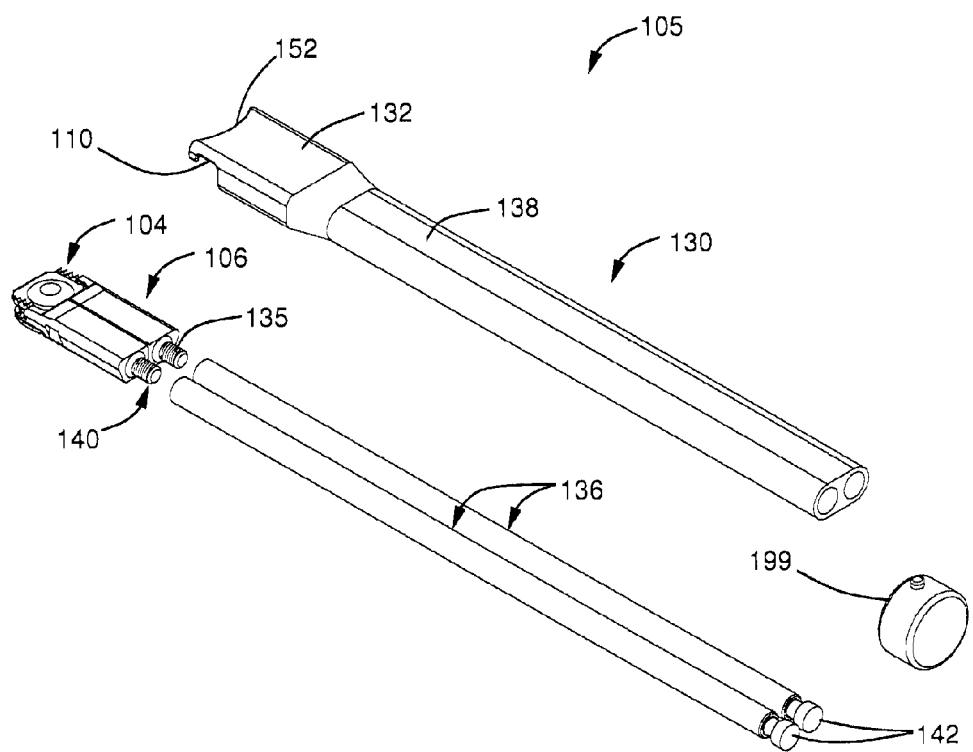
Figure 26A:
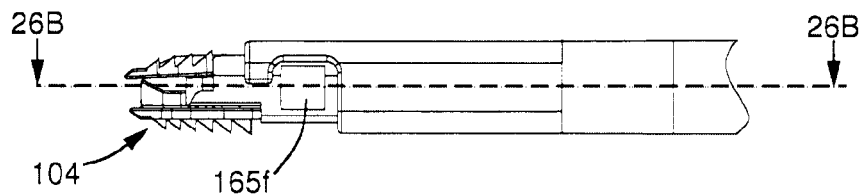
FIGS. 26A and 26B depict, respectively, a side view of a detail of the part of the prosthesis insertion assembly indicated by the reference 26A on FIG. 25A and a cross section view along cut plane (26B-26B) of the prosthesis insertion assembly of FIG. 26A, FIGS. 26C and 26D depicting, respectively, a side view of a detail of the part of the prosthesis insertion assembly indicated by reference 26C of FIG. 25A and a cross section view along cut plane (26D-26D) of the prosthesis insertion assembly of FIG. 26B.
Figure 26B:
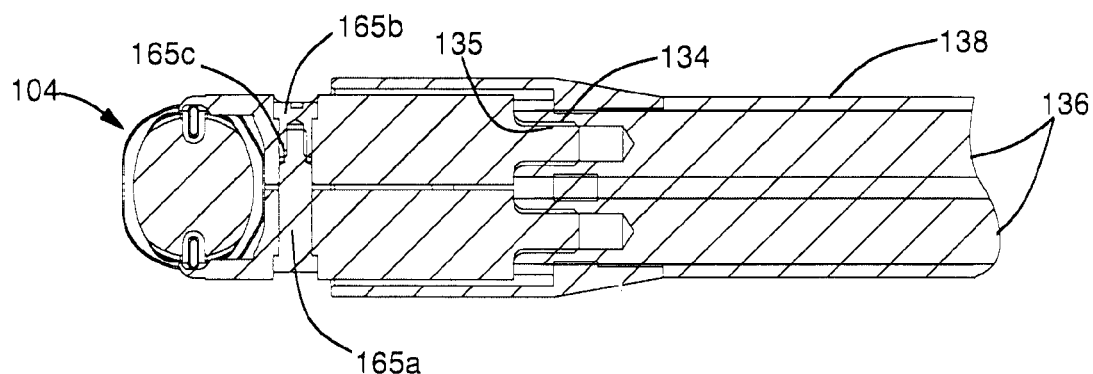
Figure 26C:
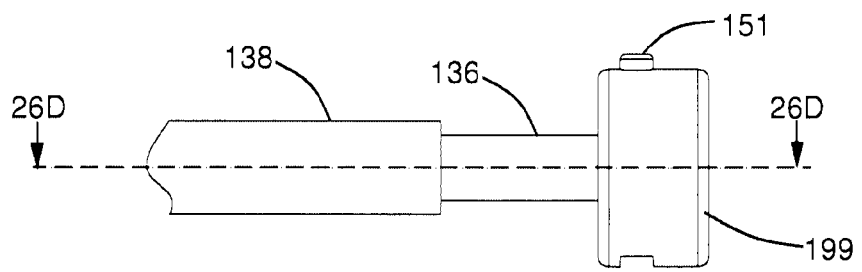
Figure 26D:
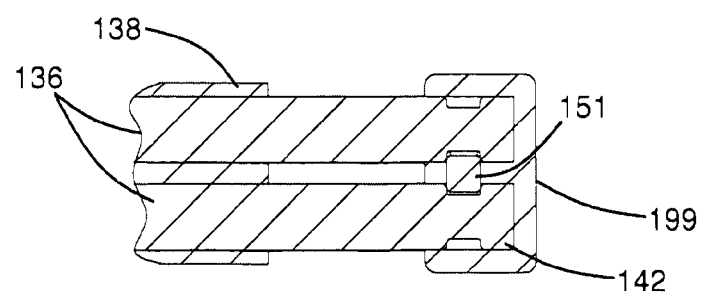

FIG. 25A shows a perspective view of an example of some embodiments of the insertion tool (131) maintaining insertion adapter (106) which body is split in two parts (164), for example such as shown on one of FIGS. 18 to 24, surrounding (holding) a prosthesis (104). The assembly formed by the prosthesis (104) held by the adapter (106) held by the insertion tool (131) can form an insertion assembly according to some embodiments of the present invention. In the embodiments of the insertion tool (131) corresponding to FIGS. 25 and 26, which are particularly suited for the embodiments of the adapter (106) of FIGS. 18 to 24, the actuating device (136) can comprise one or several rods having an end comprising a coupler (134) (such as a threaded hole for example) cooperating with the coupler(s) (140) of the adapter (such as at least one threaded rod in this example) for holding the prosthesis and having another end manipulated by the surgeon, for example thanks to a control device (142) such as a knob enabling the screwing of the actuating device (136) on the coupler of the adapter. In the embodiments shown, the actuating device(s) (136) is(are) arranged within a body (130) of the insertion tool comprising a member (138) which can be manipulated, such as an armature or a rigid envelope in which the actuator(s) (136) is(are) mounted free in rotation and in translation, so that actuating of the knob (142) allows to fix the adapter (106) on the insertion tool (131) (and reciprocally). The insertion tool (131) also comprises a support (132) comprising a housing with shape and dimensions arranged for receiving the insertion adapter (106) and comprising an edge (152) forming a stop intended to be placed in contact with at least one vertebra. It will be noted that, in these embodiments, the support (132) of the tool is not indispensable and that the edge (152) is useful for its role in indicating the position of the prosthesis in relation to the edges of the vertebrae. Thus, in some embodiments, the support (132) can be of a type which doesn't surround the adapter or can even be absent, the insertion tool (131) then comprising eventually a stop prolonging the member (138) for forming an edge (152) intended to be brought into contact with edges of the vertebrae. As shown on FIG. 25B, in some embodiments, the support (132) of the insertion tool (131) comprise, on at least one of its lateral surfaces, at least one recess (110) leaving a free access to at least lateral faces of the insertion adapter (106). Thus, as particularly visible on FIG. 26B, these recesses (110) enable accessing the swivel (165b) and/or the pin (165a) of an adapter (106) of a type such as shown on FIG. 18A for example, so that the pin can be withdrawn once the adapter is maintained by the insertion tool and before the insertion of the prosthesis (104) between vertebrae. Thus, once the prosthesis inserted between vertebrae, the adapter (106) can be easily disassembled when the insertion tool (131) is uncoupled from the adapter, while the unscrewing of the pin would have been tedious at this stage. In other embodiments, these recesses are not necessary because the pin (165a) is oriented along the longitudinal axis of the adapter (106) and can be withdrawn after the insertion of the prosthesis (104) between vertebrae. For example, in the embodiments having a pin (165a) screws in the adapter (106) by a threading (165c) inversed in relation to the threading (135) on which the actuating device (136) is screwed, the screwing of the actuating device induces the withdrawal of the pin and facilitate the release of the prosthesis by the adapter. In some embodiments, the insertion tool (131) also comprises a cap (199) mounted on an end of the actuator (136) comprising the control device (142) (or knob), so as to enable the surgeon to push on the assembly (105) and eventually strike on it (for example thanks to a tool) for inserting the prosthesis between vertebrae. As visible on FIGS. 26C and 26D, this cap (199) can comprise a ball or screw (151) enabling its fixation on one end of the actuator (136). As explained hereafter for other embodiments, in some embodiments similar to those shown on FIGS. 25 and 26, the insertion tool (131) can comprise at least one adjustable stop (144) for controlling the insertion of the prosthesis (104) inside the intervertebral space and/or a scale for indicating the position of the prosthesis (104) and/or of the adapter (106) with respect to the insertion tool (131) and/or to the vertebrae, for example thanks to the stop (152).

As shown in FIGS. 6A, 6B, and 6C, for some embodiments the actuator (136) may transit the member (138), which for example may be configured as a frame or shaft as illustrated. The actuator (136) may be equipped with a control at the end the insertion tool body (130) opposite the support (132), such as the knob (142) or a lever, button, or other control structure. In various embodiments, the control (142) may control both the delivery of the insertion adapter (106) and the prosthesis (104) to the intervertebral disc space from the support (132) as well as the release of the insertion adapter (106) from the insertion tool body (130) following such delivery, but separate controls may be provided for each function, and optionally may be provided for other functions. For insertion of the prosthesis (104) in various embodiments, the rod (136) may slide in the member (138) of the insertion tool body (130) toward the support (132) (the insertion direction), thus moving the insertion assembly (100) into the intervertebral disc space. With the insertion assembly (100) moved into the intervertebral disc space, threaded end (134) of rod (136) may be decoupled from the coupler of the insertion adapter (106) and the insertion tool body (130) moved away.

Various embodiments of the insertion tool body (130) may preferably be configured with an adjustable insertion stop to control the distance of the insertion of the intervertebral prosthesis (104) within the intervertebral disc space. FIGS. 6A, 6B, and 6C depict an exemplary adjustable stop configuration. In FIG. 6A, the prosthesis insertion assembly (100) is fully disposed in and firmly retained by support (132), with the threaded end (134) being substantially or fully engaged with threaded hole (140). A scale (147) may be disposed on a planar recess disposed on a shaft or stud (141) integral with or attached to the control knob (142). The scale (147) may be graduated in appropriate units of length and may include a zero mark (148). Tangs (164) and threaded hole (140) of insertion adapter (106) may be dimensioned and configured to accommodate further rotation of threaded end (134) in the threaded hole (140) in the position illustrated by FIG. 6A. Knob (142) may can be adjusted in handle (139) to position the zero mark (147) at an appropriate indicator, such as the end of handle (139) or other form of reference, for example as illustrated in FIG. 6B, which indexes knob (142), shaft or stud (141), rod (136), and the prosthesis insertion assembly (100) in the fully mounted position in support (132).

For various embodiments, when the zero mark (148) is set to the indicator with the prosthesis insertion assembly (100) in the fully mounted position in the support (132), for example as depicted in FIG. 6B, the scale (147) will indicate the distance that the prosthesis insertion assembly (100) has been extended from the support (132) by movement of the rod (136) within member (138) of insertion tool body (130). During the insertion of the intervertebral disc prosthesis (104), the leading edges (152) of the support (132) may be held firmly against respective vertebrae (150) defining the disc space receiving the prosthesis (104), as illustrated for example in FIGS. 8 and 10. Accordingly, the scale (147) can be used to indicate the distance of insertion of the prosthesis (104) within the intervertebral disc space.

Various embodiments may deploy an adjustable stop, for example a threaded nut (144) adjustable along threads (137) of the shaft or stud (141). The adjustable stop (144) may be used to control the distance of insertion of the prosthesis (104) within the intervertebral disc space. In various embodiments, for example, sliding of the rod (136) in the insertion direction will be stopped when the adjustable stop (144) abuts the end of handle (139). A stop lock may be used to maintain the setting of the stop (144), for example by use of a lock nut (146) as illustrated, or by other known locking structures. Preferably, the stop (144) will be adjusted in accordance with the size of the intervertebral disc space, typically measured and analyzed before the insertion stage of the surgical procedure as discussed elsewhere in this disclosure. FIG. 6C depicts an insertion assembly (100) extended from support (132) by a distance controlled by stop (144) abutting handle (139).

Figure 7:
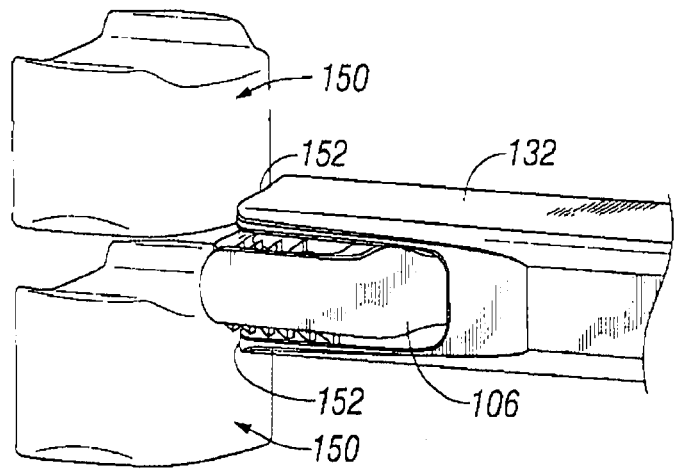
FIG. 7 depicts an embodiment of a prosthesis insertion assembly and a support of an insertion tool body.
Figure 8:
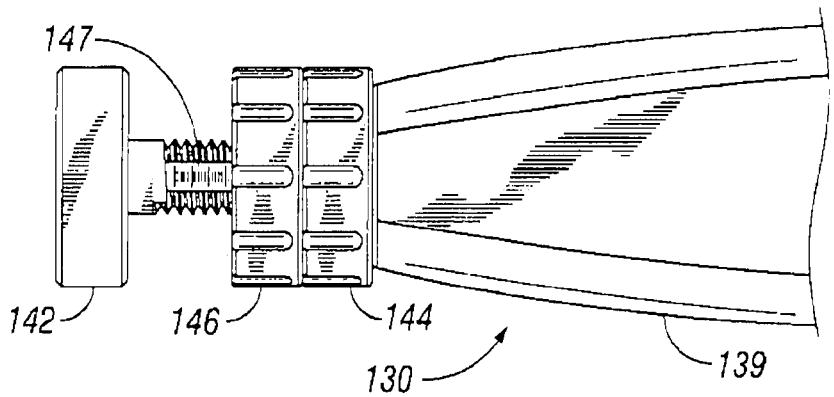
FIG. 8 depicts components and a portion of an embodiment of an insertion tool body.
Figure 9:
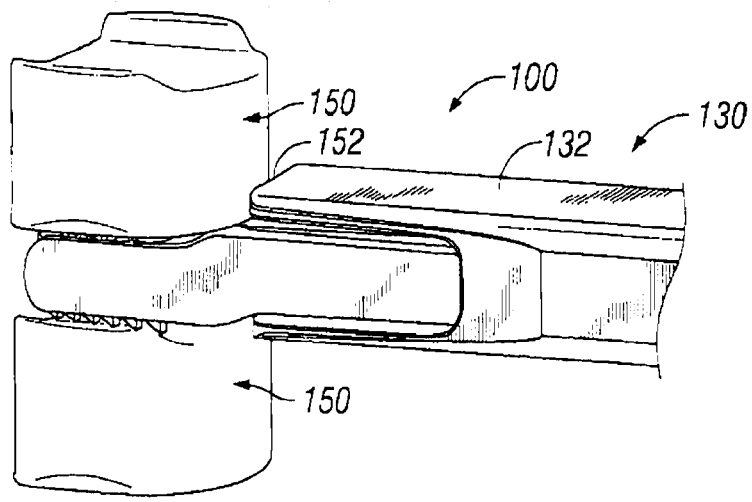
FIG. 9 depicts an embodiment of a prosthesis insertion assembly and a support of an insertion tool body.
Figure 10:
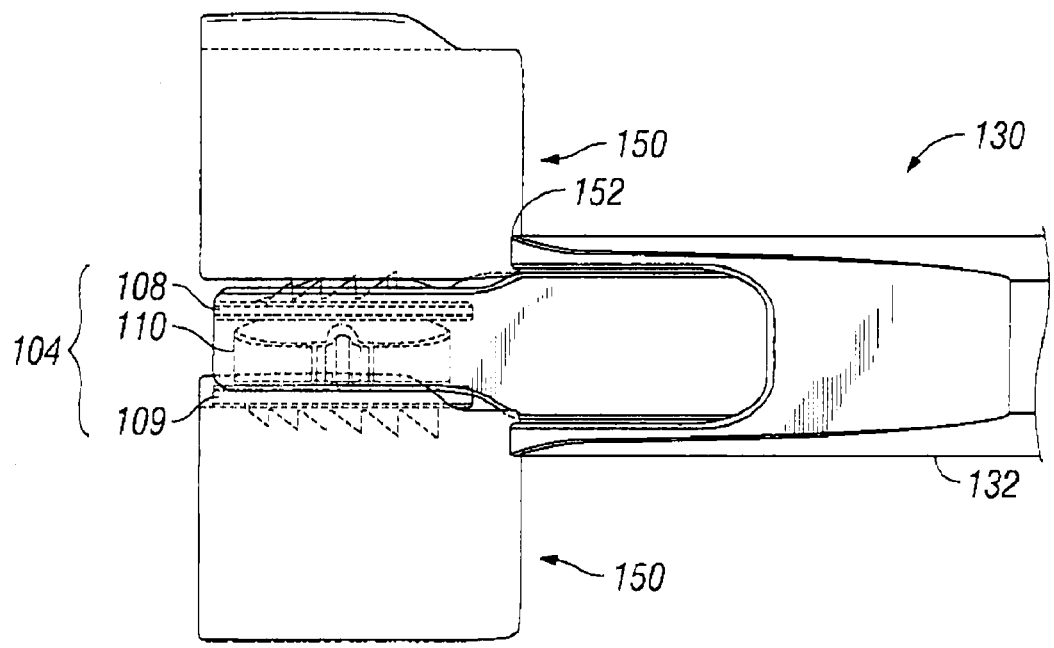
FIG. 10 depicts an embodiment of a prosthesis insertion assembly and a support of an insertion tool body.

FIG. 7 illustrates the commencement of the insertion stage of an embodiment of a surgical procedure. The insertion tool (130) and the prosthesis insertion assembly (100) may be configured and adjusted in accordance with the discussion above. The insertion tool (130) and the insertion assembly (100) may be located in the desired prosthesis insertion axis and located to place the leading edges (152) of the support (132) in contact with the respective vertebrae (150) defining the intervertebral disc space receiving the prosthesis (104). In various embodiments, the surgeon may apply force to the knob (142) by pressing it or striking it with a soft mallet or by hand. Force may be applied until the stop (144) abuts the end of the handle (139), as shown in FIG. 8. When the stop (144) abuts the end of the handle (139), the end (134) of the rod (136) will have pushed the insertion adapter (106) into position where the prosthesis (104) is properly positioned in the intervertebral disc space between the vertebrae (150). FIGS. 9 and 10 provide a representative illustration of the final positioning at this stage.

Figure 11:
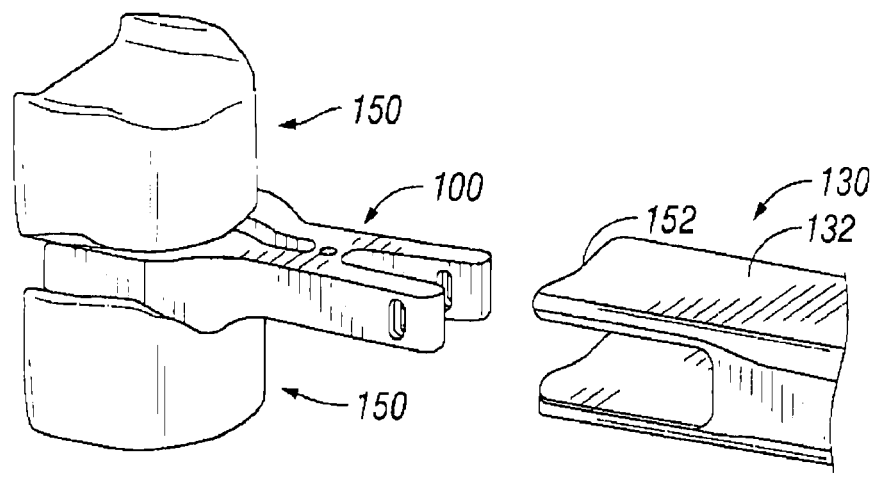
FIG. 11 depicts an embodiment of a prosthesis insertion assembly and a support of an insertion tool body.
Figure 12:
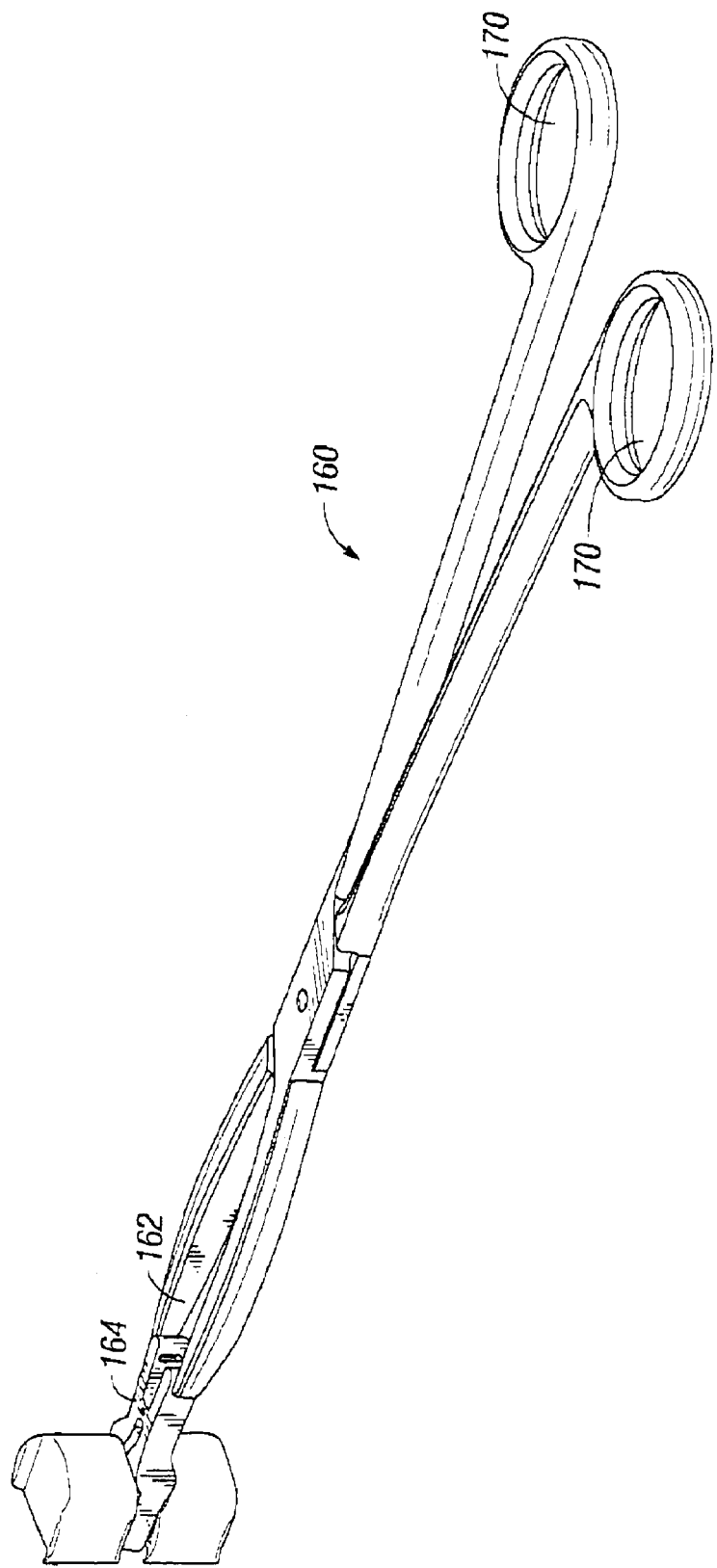
FIG. 12 depicts an embodiment of a removal tool.
Figure 13:
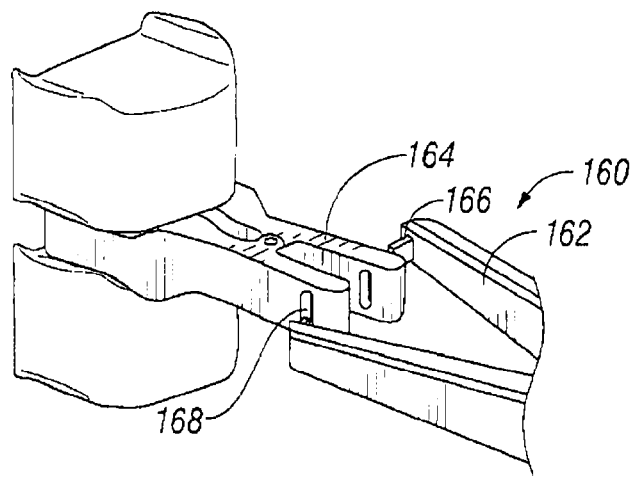
FIG. 13 depicts an embodiment of a prosthesis insertion assembly and a removal tool.
Figure 14:
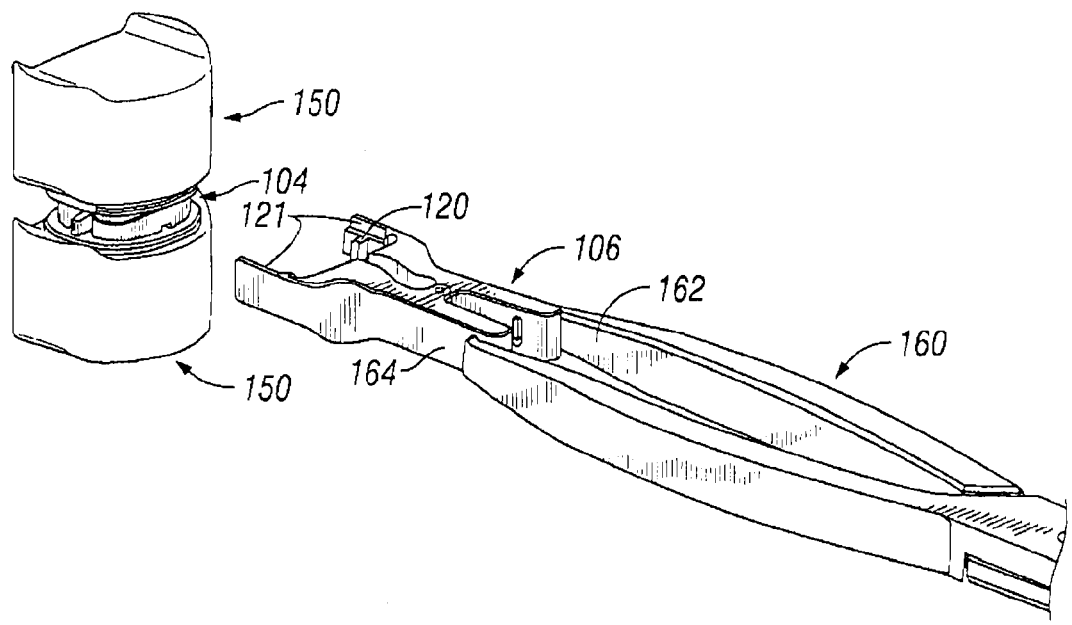
FIG. 14 depicts an embodiment of an intervertebral disc prosthesis, an insertion adapter, and a removal tool.

For various embodiments, the insertion tool body (130) may be detached or demounted from the insertion assembly (100) by rotating the knob (142) counter-clockwise until the threaded end (134) releases from the threaded hole (140). FIG. 11 shows the insertion tool body (130) as it is being withdrawn, leaving only the insertion assembly (100) in the opening between the vertebrae (150). A removal tool (160), for example as shown in FIG. 12, may be used to separate the insertion adapter (106) from the prosthesis 104, leaving the prosthesis (104) implanted in the intervertebral disc space. FIG. 13 shows the removal tool (160) approaching the insertion adapter (106). Tool ends (162) of the removal tool (160) may be positioned along the tangs (164) of the insertion adapter (106) in such a way that pins (166) enter slots (168) disposed in the tangs (164). Other embodiments may include a single hole in each tang (164), multiple smaller holes or slots, or any of many other means for the removal tool (160) to attach with, connect to, or latch on the tangs (164) of the insertion adapter (106). Actuating a removal tool (160) by squeezing handles (170) of the removal tool (160) may pivot the tangs (164) of the insertion adapter (106) around the hinge pin (172), causing the jaws (121) to release the plates and the mounting dogs (120) to release their grip on the posts (124) and disengage from the recesses (122). In alternative embodiments of insertion adapter (106) comprising a flexible portion at which the tangs (164) articulate, squeezing the tangs (164) will cause the flexible body to flex, the tangs (164) to articulate, the jaws (121) to release the plates, and the mounting dogs (120) to release their grip on the posts (124) and disengage from the recesses (122). Once the insertion adapter (106) releases the prosthesis (104), the insertion adapter (106) may be removed, for example as shown in FIG. 14, leaving the prosthesis (104) properly positioned in the disc space between the two vertebrae (150).

Figure 15:
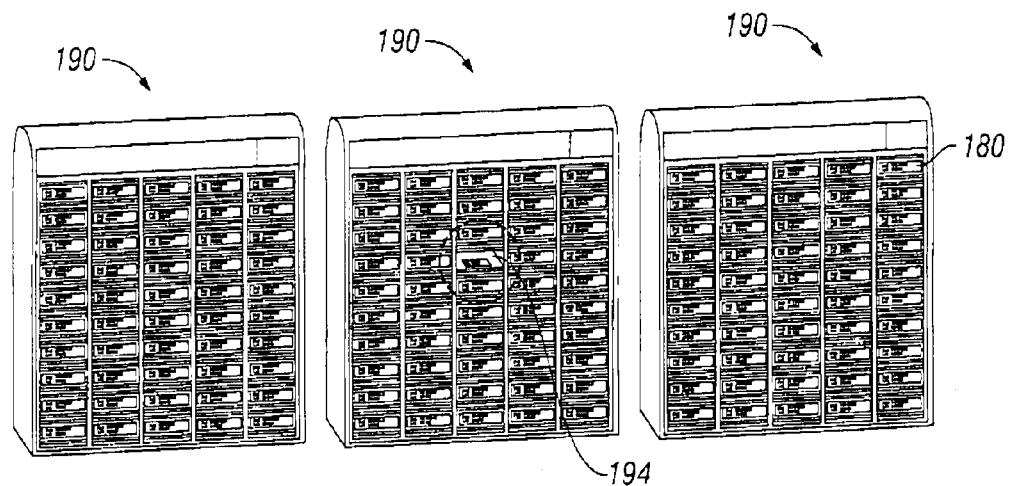
FIG. 15 depicts an embodiment of inventory storage space and a storage location.

Various embodiments of an intervertebral disc prosthesis delivery and insertion system also maybe provided. In a preferred embodiment, the sterile pack (102) inventory may be maintained in dedicated inventory storage space, for example racks (190) as illustrated in FIG. 15. Various embodiments may have prostheses each configured with a first plate having a size and configuration selected from a set of first size and configuration specifications, a second plate having a size and configuration selected from a set of second size and configuration specifications, and a core having a size and configuration selected from a set of third size and configuration specifications. The first plate, the second plate, and/or the core configuration optionally may specify a lordosis or kyphosis correction. In various embodiments, any of the sets of size and configuration specifications may contain only one element, in which case the particular component may be provided in only one size and configuration.

Preferably, the inventory will be organized by plate dimension, core height, and lordosis/kyphosis correction angle (if any), but other characteristics of the prostheses (104) may be used for an organizational scheme. Each rack (190), for example, may contain insertion assemblies (100) of various dimensions all having a particular lordosis/kyphosis correction angle, with the sterile packs (102) organized in the respective racks (190) in rows by the plate dimension and in columns by the core height of the packaged prostheses (104). Alternatively, any organization scheme using any combination of the set of first size and configuration specifications, the set of second size and configuration specifications, and/or the third size and configuration specifications may be used. Preferably, each storage location (194) corresponds to one of the selected combinations of first size and configuration specifications, second size and configuration specifications, and/or third size and configuration specifications.

As noted above, in various embodiments the sterile packs (102) of insertion assemblies (100) preferably bear identifying information. For example, various embodiments optionally have a package label (198, FIG. 16) with identifying information (180). The label (180) disposed on a sterile pack (102) preferably will indicate the enclosed prosthesis's plate dimension, core height, and lordosis/kyphosis correction angle (if any), along with the stock-keeping unit (SKU) designation of the sterile pack (102) and the other information discussed above, some or all of which preferably may be encoded in scannable code included on the label or other component of the packaging, for example a chip or transponder. Other information (180) optionally may be provided, for example further logistical management information such as inspection data, reorder points, lead times, etc., or information relevant to surgical techniques and equipment. Coding can be done with bar or other optical codes, magnetic stripes, radio-frequency identification, or other known techniques. The identifying information (180) on a sterile pack (102) preferably may be readable when insertion assembly (100) is stocked in the rack.

Figure 16:
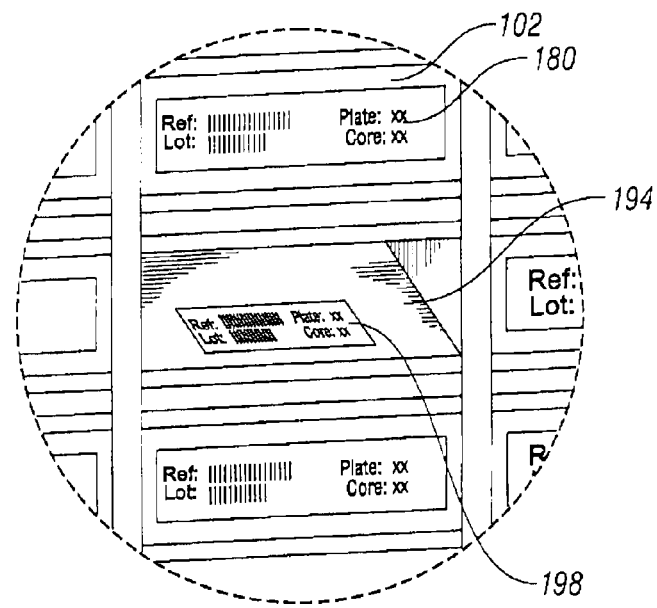
FIG. 16 depicts an embodiment of a storage location and configuration information.

The sterile pack (102) storage locations, for example bins (194) of the racks (190), optionally each may contain a label having identifying information for the sterile pack (102) that should be stocked in that bin (194), for example as depicted in FIG. 16. Other means of providing the information about the sterile pack (102) that should be stored in the bin (194), of course, may be use, for example magnetic stripes, radio-frequency identification, or other known techniques. Preferably, each bin label (194) or other form of identifying information may be readable when the respective bin (194) is empty. Thus, stock keeping may be simplified by providing sufficient information for re-ordering from routine observation of empty rack spaces, and acquisition of the correct assembly (100) during surgery may be simplified by the rack's organizational scheme. Stock keeping and insertion assembly (100) acquisition can be further enhanced by providing label- or other information-scanning equipment in the sterile field of the surgical suite, which will provide another level of verification of sterile pack (102) ordering and acquisition.

After appreciating this disclosure, those of skill in the art will recognize that other logistical management techniques advantageously can be applied to the intervertebral disc prosthesis delivery and insertion systems and methods disclosed herein.

Figure 17:
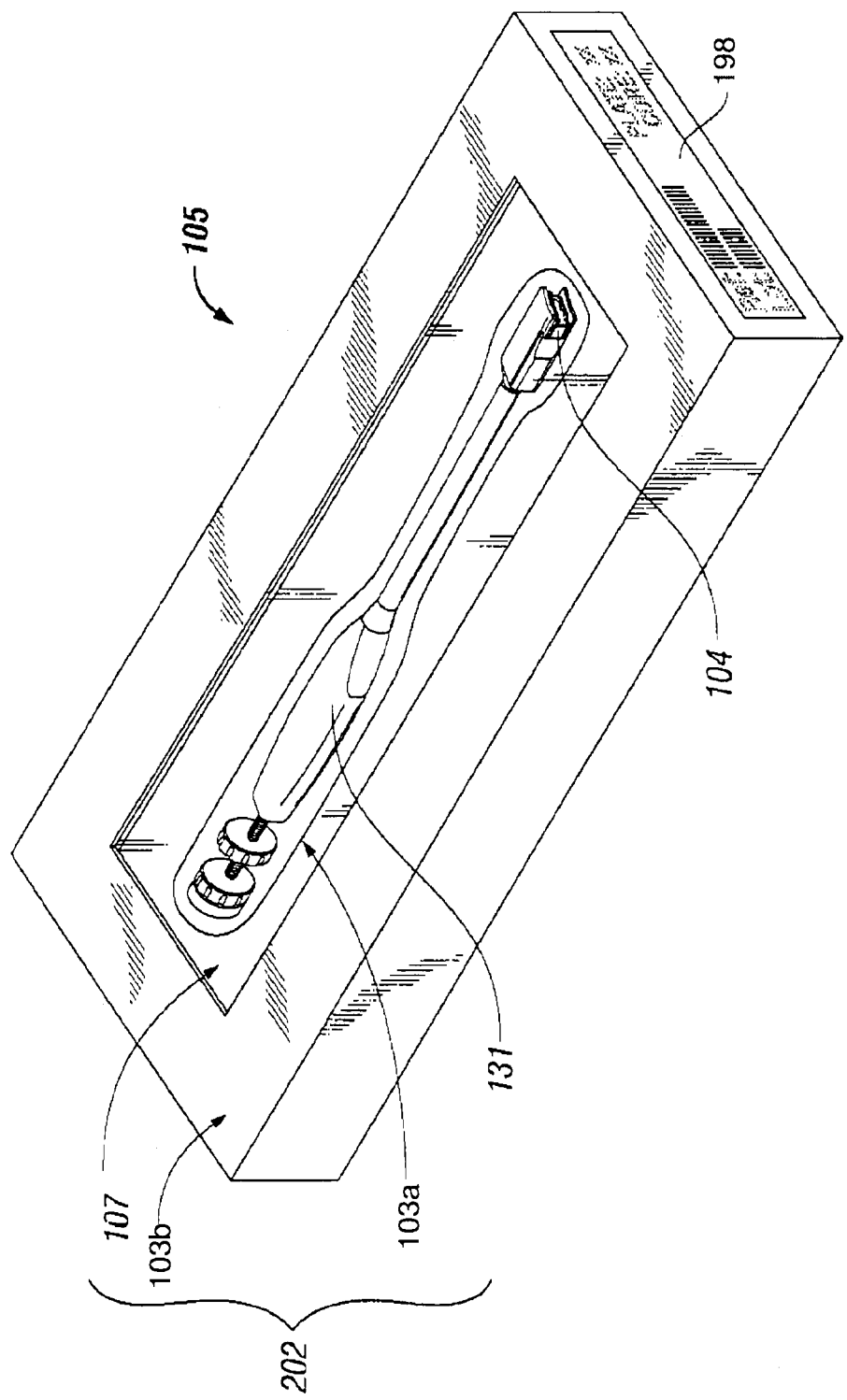
FIG. 17 depicts an embodiment of a sterile pack comprising a prosthesis insertion assembly.

Various features of embodiments of a packaged intervertebral disc prosthesis insertion assembly (101) comprising a sterile insertion adapter (106) and sterile components of n intervertebral disc prosthesis (104) are described above. Those of skill in the art will recognize after appreciating this disclosure that similar features may be provided in embodiments of a packaged intervertebral disc prosthesis insertion assembly (105) comprising a sterile insertion tool (131) and sterile components of an intervertebral disc prosthesis (104). For example, as shown in FIG. 17 the sterile insertion tool (131) and the sterile intervertebral disc prosthesis (104) may be assembled together and disposed in primary, or inner, sterile packaging (103a) and in secondary, or outer, sterile packaging (103b) to form a sterile pack (202). The components of the intervertebral disc prosthesis (104) in this embodiment maybe assembled with the sterile insertion tool (131) and provided to the sterile field of a surgical suite pre-configured and ready to use. The sterile insertion tool (131) optionally may have an insertion tool body (130) and a detachable insertion adapter (106), which may be packaged, assembled or disassembled. Alternatively, the sterile insertion tool (131) may have an insertion adapter (106) integral with an insertion tool body (130), or the sterile insertion tool (131) may have other structures devised to hold the intervertebral disc prosthesis (104) and/or deliver it to the intervertebral disc space. Various features of the insertion adapter (106) and/or the insertion tool body (130) discussed above, and/or the various components of the foregoing and other components discussed above, optionally may be included for the packaged intervertebral disc prosthesis insertion assembly (105). Various features the intervertebral disc prosthesis delivery and insertion systems discussed above, as well as features of other systems, optionally may also be used with a packaged intervertebral disc prosthesis insertion assembly (105) comprising a sterile insertion tool (131) and sterile components of an intervertebral disc prosthesis (104).

Those of skill in the art will recognize after appreciating this disclosure that the steps of the various methods, processes, and other techniques disclosed herein need not be performed in any particular order, unless otherwise expressly stated or logically necessary to satisfy expressly stated antecedent conditions. In addition, after appreciating this disclosure those skilled in the art will recognize that the invention may be embodied in a variety of different forms and that various changes, substitutions, and alterations can be made without departing from the spirit and scope of the invention. The described embodiments are illustrative only and are not restrictive, and the scope of the invention is defined solely by the following claims.

The invention claimed is:

1. An intervertebral disc prosthesis insertion assembly comprising:
    an insertion adapter disposed in sterile packaging and comprising an operationally releasable coupler for a demountable insertion tool body, an intervertebral disc prosthesis configured to be releasably retained by the insertion adapter, at least two component parts configured to be releasably tightened around at least part of the prosthesis, and at least one retainer that engages a recess or a post of the intervertebral disc prosthesis; and
    an insertion tool disposed in sterile packaging and comprising a demountable insertion tool body configured for releasable mounting of the coupler, and an insertion actuator having a rod with a threaded end configured for rotation in a threaded hole of the insertion adaptor to draw the prosthesis insertion assembly within and retain the prosthesis insertion assembly in the insertion tool.

2. An intervertebral disc prosthesis insertion assembly according to claim 1, in which the at least two component parts are arranged to release the intervertebral disc prosthesis by pivoting one in relation to the other.

3. An intervertebral disc prosthesis insertion assembly according to claim 1, in which the insertion adapter has a surface complementary to and substantially fitting the intervertebral disc prosthesis.

4. An intervertebral disc prosthesis insertion assembly according to claim 1, in which the retainer is a latch, and the recess is disposed on an edge of a plate of the intervertebral disc prosthesis.

5. An intervertebral disc prosthesis insertion assembly according to claim 1, in which the retainer is a dog, and the recess is disposed along a core of the intervertebral disc prosthesis.

6. An intervertebral disc prosthesis insertion assembly according to claim 5, in which the dog has a channel substantially matching the edge of a post of a plate of the intervertebral disc prosthesis.

7. An intervertebral disc prosthesis insertion system according to claim 1, in which the insertion tool body comprises an insertion stop.

8. An intervertebral disc prosthesis insertion system according to claim 7, in that in which the insertion tool body comprises an insertion stop lock.

9. An intervertebral disc prosthesis insertion system according to claim 8, in which the insertion stop lock is adjustable.

10. An intervertebral disc prosthesis insertion system according to claim 9, in which the intervertebral disc prosthesis comprises a first plate, a second plate and a core.

11. An intervertebral disc prosthesis insertion assembly comprising:
    an insertion adapter comprising an operationally releasable coupler for a demountable insertion tool body, an intervertebral disc prosthesis releasably retained by the insertion adapter, and at least two component parts configured to be releasably tightened around at least part of the prosthesis;
    an insertion tool comprising a demountable insertion tool body configured to be releasably mounted to the coupler, and an insertion actuator having a rod with a threaded end configured to draw the prosthesis insertion assembly within the insertion tool and retain the prosthesis insertion assembly in the insertion tool; and an insertion adapter removal tool having a handle configured for squeezing to separate the insertion adaptor from the prosthesis.

12. An intervertebral disc prosthesis insertion assembly according to claim 11, in which the at least two component parts are arranged to release the intervertebral disc prosthesis by pivoting one in relation to the other.

13. An intervertebral disc prosthesis insertion assembly according to one of claim 12, in which the insertion adapter and the intervertebral disc prosthesis are disposed in sterile packaging to form a sterile pack.

14. An intervertebral disc prosthesis insertion assembly according to one of claim 12, in which the insertion adapter has a surface complementary to and substantially fitting the intervertebral disc prosthesis.

15. An intervertebral disc prosthesis insertion assembly according to claim 11, in which the insertion adapter has at least one retainer that engages a recess and/or a post of the intervertebral disc prosthesis.

16. An intervertebral disc prosthesis insertion assembly according to claim 15, in which the retainer is a latch, and the recess is disposed on an edge of a plate of the intervertebral disc prosthesis.

17. An intervertebral disc prosthesis insertion assembly according to one of claim 16, in which the retainer is a dog, and the recess is disposed along a core of the intervertebral disc prosthesis.

18. An intervertebral disc prosthesis insertion assembly according to claim 17, in which the dog has a channel substantially matching the edge of a post of a plate of the intervertebral disc prosthesis.

19. An intervertebral disc prosthesis insertion system according to claim 11, in which the insertion tool body comprises an insertion stop.

20. An intervertebral disc prosthesis insertion system according to claim 19, in which the insertion tool body comprises an insertion stop lock.

* * * * *